(12) United States Patent
Merz et al.

(10) Patent No.: US 8,801,917 B2
(45) Date of Patent: Aug. 12, 2014

(54) ELECTROCHEMICAL POTENTIOMETRIC SENSING WITHOUT REFERENCE ELECTRODE

(75) Inventors: Matthias Merz, Leuven (BE); Youri Victorovitch Ponomarev, Leuven (BE); Gilberto Curatola, Korbek-lo (BE)

(73) Assignee: NXP, B.V., Eindhoven (NL)

( * ) Notice: Subject to any disclaimer, the term of this patent is extended or adjusted under 35 U.S.C. 154(b) by 477 days.

(21) Appl. No.: 13/061,110

(22) PCT Filed: Aug. 24, 2009

(86) PCT No.: PCT/IB2009/053710
§ 371 (c)(1),
(2), (4) Date: May 13, 2011

(87) PCT Pub. No.: WO2010/023611
PCT Pub. Date: Mar. 4, 2010

(65) Prior Publication Data
US 2011/0208457 A1      Aug. 25, 2011

(30) Foreign Application Priority Data

Aug. 25, 2008   (EP) ..................................... 08105116
Aug. 25, 2008   (EP) ..................................... 08105117

(51) Int. Cl.
*G01N 27/327*      (2006.01)

(52) U.S. Cl.
USPC ..................... 205/777.5; 204/403.01; 204/408

(58) Field of Classification Search
USPC ............... 205/787.5, 789, 777.5; 204/403.01, 204/416–419, 433, 408; 257/253; 324/438
See application file for complete search history.

(56) References Cited

U.S. PATENT DOCUMENTS 4,133,735  A  *  1/1979  Afromowitz et al. .......... 204/406
4,490,678  A  *  12/1984  Kuisl et al. ..................... 324/438
(Continued)

FOREIGN PATENT DOCUMENTS

CN           101163965 A       4/2008
EP           1 471 349 A2      10/2004
(Continued)

OTHER PUBLICATIONS

Derwent English language translation of the abstract of Hanaoka et al. JP 54-106294 A, patetn published Aug. 21, 1979.*

(Continued)

*Primary Examiner* — Alex Noguerola

(57) ABSTRACT

The invention relates to a method of determining a charged particle concentration in an analyte (100), the method comprising steps of: i) determining at least two measurement points of a surface-potential versus interface-temperature curve (c1, c2, c3, c4), wherein the interface temperature is obtained from a temperature difference between a first interface between a first ion-sensitive dielectric (Fsd) and the analyte (100) and a second interface between a second ion-sensitive dielectric (Ssd) and the analyte (100), and wherein the surface-potential is obtained from a potential difference between a first electrode (Fe) and a second electrode (Se) onto which said first ion-sensitive dielectric (Fsd) and said second ion-sensitive dielectric (Ssd) are respectively provided, And ii) calculating the charged particle concentration from locations of the at least two measurement points of said curve (c1, c2, c3, c4). This method, which still is a potentiometric electrochemical measurement, exploits the temperature dependency of a surface-potential of an ion-sensitive dielectric in an analyte. The invention further provides an electrochemical sensor for determining a charged particle concentration in an analyte. The invention also provides various sensors which can be used to determine the charged particle concentration, i.e. EGFET's and EIS capacitors.

22 Claims, 8 Drawing Sheets

(56) References Cited

U.S. PATENT DOCUMENTS

| | | | |
|---|---|---|---|
| 4,716,448 A | | 12/1987 | Kelly |
| 5,071,537 A | | 12/1991 | Yamaguchi et al. |
| 5,236,568 A | * | 8/1993 | Steiner ............... 204/406 |
| 5,320,735 A | * | 6/1994 | Kato et al. ............ 204/419 |
| 6,090,249 A | | 7/2000 | Guth |
| 6,963,193 B2 | | 11/2005 | Chou et al. |
| 7,011,735 B1 | | 3/2006 | Neumann ............. 204/427 |
| 7,972,494 B2 | * | 7/2011 | Tam ..................... 205/777.5 |
| 2008/0067081 A1 | * | 3/2008 | Chou et al. ............ 205/787.5 |
| 2008/0257731 A1 | | 10/2008 | Cramer et al. ........ 204/425 |

FOREIGN PATENT DOCUMENTS

| | | | |
|---|---|---|---|
| GB | 2 088 565 | | 6/1982 |
| GB | 2341235 A | | 3/2000 |
| JP | 54-106294 A | * | 8/1979 ......... G01N 27/416 |

OTHER PUBLICATIONS

Zerihun, T., et al. "Electrically Heated Cylindrical Microelectrodes. The Reduction of Dissolved Oxygen on Pt," Journal of Electroanalytical Chemistry and Interfacialelectro Chemistry, Elsevier, Amsterdam, NL, vol. 404, No. 2, pp. 243-248, (Mar. 21, 1996).

Klein, M., "Characterization of Ion-Sensitive Layer Systems With A V(V) Measurement Method of Operating at Constant Capacitance," Sensors and Actuators B1, pp. 354-356, (1990).

Bergveld, P.: "Thirty Years of Isfetology What Happened in the Past 30 Years and What may Happen in the Next 30 Years," Sensors and Actuators, B 88, pp. 1-20, (2002).

Jamasb, S.: "Analytical Technique for Counteracting Drift in Ion-Selective Field Effect Transistors (ISFETs)," IEEE Sensors Journal, vol. 4, No. 6, pp. 795-801, (Dec. 2004).

Yoshida, S., et al.,: "Development of a Wide Range pH Sensor based on Electrolyte-Insulator Semiconductor Structure with Corrosion-Resistant $Al_2O_3$-Ta2O5 and $Al_2O_3$-$ZrO_2$ Double-Oxide Thin Films," Journal of the Electrochemical Society, vol. 151, No. 3, pp. 53-58, (2004).

Ylén, J-P, "Measuring, Modeling, and Controlling the PH-Value and the Dynamic Chemical State," Helsinki University of Technology, Control Engineering Laboratory, Report 127, pp. 1-164, (2001).

International Search Report for Int'l. Patent Appln. No. PCT/IB2009/053710.

Office action from counterpart application CN 200980133184.6 Dec. 13, 2012.

* cited by examiner (1) $\varphi = (k*T/(n*q))*\ln(a_1/a_2)$ $= (k*T/(n*q))*(\ln a_1 - \ln a_2)$ $= \ln 10 * (k*T/(n*q)) * (\log a_1 - \log a_2)$ $= \ln 10 * (k*T/(n*q)) * (\mathbf{pa_2 - pa_1}) \approx$ $= 2.3 * (k*T/(n*q)) * (\mathbf{pa2 - pa1})$ (2) $\Delta\varphi = \varphi_m - \varphi_{ref}$ (3a) $\Delta\varphi = 2.3 * k*T/q * (pHin - pHout) + (\varphi_{cont} - \varphi_{ref})$ (3b) $\Delta\varphi = 2.3 * k*T/q * \alpha * (pHpzc - pH) - \varphi_{ref}$

Fig. 1

(4a) $\Delta\varphi = 2.3*k*T/q*(pHin - pHout) + \varphi_{cont} - \varphi_{ref}$
$= m*T + \varphi_{cont} - \varphi_{ref}$ (4b) $m = 2.3*k/q*(pHin - pHout)$ (4c) → $pHout = pHin - m*q/(k*2.3)$ (5a) $\Delta\varphi = 2.3*k*T/q*\alpha*(pHpzc - pHout) - \varphi_{ref}$
$= m*T - \varphi_{ref}$ (5b) $m = 2.3*k/q*\alpha*(pHpzc - pHout)$ (5c) → $pHout = pHpzc - m*q/(\alpha*k*2.3)$ (6) $\alpha = \dfrac{1}{\dfrac{2.3kC_S}{q^2\beta_S}T + 1}$ (7a) $\Delta\varphi = 2.3*k*T_{fe}/q*\alpha_{fe}*(pHpzc_{fe} - pHout)$
$- 2.3*k*T_{se}/q*\alpha_{se}*(pHpzc_{se} - pHout)$ (7b) $\Delta\varphi = 2.3*k/q*\alpha*(pHpzc - pHout)(T_{fe} - T_{se}) = m*\Delta T$

Fig. 3

ELECTROCHEMICAL POTENTIOMETRIC SENSING WITHOUT REFERENCE ELECTRODE

FIELD OF THE INVENTION

The invention relates to an electrochemical sensor for determining a charged particle concentration in an analyte, a semiconductor device comprising such sensor, an RF-ID tag comprising such sensor, and to a method of determining a charged particle concentration in an analyte.

BACKGROUND OF THE INVENTION

The pH-value is an integral parameter of every (aqueous) solution. It describes to which degree the solution is alkaline or acidic. Over a wide range it is well approximated by: $pH=-\log_{10}[H^+]$, wherein $[H^+]$ denotes the hydrogen ion concentration of the solution in mol/L. Measuring a pH-value of an aqueous solution is a routine task in the industry and also in laboratories for process control and analysis. However, it could also become interesting for a wider range of applications if the pH-measurement units (sensor plus electronics) become sufficiently inexpensive. For example, there is a large potential for pH-measurement to monitor the quality of (liquid) perishables in the supply chain or even at the customer's himself. Experimental techniques for measuring ion concentrations (in particular pH) can be divided into two classes, non-electrochemical methods, e.g. optical (indicator dyes), catalytic, and swelling of polymers (gels), and electrochemical methods. The latter are widely used for many applications in industry and laboratories. Electrochemical ion concentration sensors rely on the potentiometric principle, i.e. they measure the electrical potential $\phi$ at a solid/liquid interface or across a membrane which is a function of the ion concentration to be determined. $\phi$ can be calculated from the Nernst equation: $\phi=kT/(nq) \ln(a_1/a_2)$, wherein k is the Boltzmann constant, T the absolute temperature in Kelvin, q the elementary charge, n the ionic charge (e.g., n=1 for $H_3O^+$, $Na^+$; n=2 for $Ca^{2+}$), and $a_1$, $a_2$ the respective activities at both sides of the membrane/interface.

Ion concentrations at both sides of the membrane/interface are represented in terms of activities $a_i=f_i*c_i$ with $f_i$ being the respective activity coefficient ($f_i=1$ for diluted electrolytes) and $c_i$ the respective ion concentration. According to the Nernst equation the electrode potential is a logarithmic function of the ion activity on one side of the membrane/interface if the activity on the other side is kept constant. Depending on the type of ion described by "a", the sensor is sensitive to $H_3O^+$-ions, $Na^+$-ions, $Ca^{2+}$-ions, etc.

All major pH (ion) measurement electrodes operate according to the principle described above, including the well-known glass electrodes (different glass compositions have been developed that are sensitive to pH, pNa, pK, etc., respectively), antimony electrodes, ISFET's (Ion Sensitive Field Effect Transistors) and EIS capacitors (Electrolyte Insulator Semiconductor capacitors; here the flat-band voltage is a function of the pH/pNa/pK/etc of the electrolyte).

In order to measure the potential difference a reference electrode is needed; for the ISFETS and EIS devices the reference electrode defines the electrolyte potential to set the operating point and do the measurement. The potential of the reference electrode with respect to the electrolyte potential must remain constant irrespective of the electrolyte composition. Besides the standard hydrogen electrode the Ag/AgCl electrode is the most well-known reference electrode. It consists of a chlorinated silver wire in contact with a well defined electrolyte (often 3 mol/L KCl). Galvanic contact between the analyte and the electrolyte is established via a diaphragm, such as a porous frit from glass or ceramics. During operation the electrolyte must continuously flow out of the reference electrode into the analyte. Other reference electrodes, e.g. calomel (based on mercury) or Tl/TlCl electrodes, are used for specific applications, e.g. at elevated temperatures. Their principle is the same as for the Ag/AgCl electrode, in particular with respect to the use of liquid electrolyte and contact via a diaphragm.

The problem with the known electrochemical sensors is that they require a reference electrode in order to determine the charged particle concentration from a measured potential (difference). Using reference electrodes, and in particular accurate reference electrodes, involves all kinds of difficulties such as the following:

Electrolyte outflow in a reference electrode through the diaphragm is essential. That means the electrolyte needs to be refilled regularly. Moreover, the pressure conditions must be such that the outflow is guaranteed, i.e. the pressure in the analyte cannot be higher than in the reference electrode (otherwise the analyte enters the reference electrode and changes its potential, which is called reference electrode poisoning;

Clogging of the diaphragm of the reference electrode causes measurement errors (depending on the application regular cleaning is needed);

Most reference electrodes have rather large dimensions, which makes it difficult/impossible to integrate them into a miniaturized device. Some miniature reference electrodes exist but they have a limited lifetime (because reference electrolyte cannot be refilled);

Reference electrodes have a limited temperature range, e.g., for high temperatures a Tl/TlCl electrode must be used; and Some reference electrodes may react to other environmental parameters, for example, the silver in Ag/AgCl electrodes is light sensitive.

Even pseudo-reference electrodes suffer from several disadvantages, such as:

complex (expensive) integration, corrosion, interface leakage, food and bio-compatibility issues.

SUMMARY OF THE INVENTION

It is an object of the invention to provide an electrochemical sensor for determining a charged particle concentration, which does not require a conventional reference electrode or a pseudo-reference electrode.

The invention is defined by the independent claims. The dependent claims define advantageous embodiments.

In a first aspect, the invention relates to an electrochemical sensor for determining a charged particle concentration in an analyte, the sensor comprising:

a first electrode with a first ion-sensitive dielectric provided thereon, the first electrode being arranged for contacting the analyte via the first ion-sensitive dielectric to obtain a first interface between the first ion-sensitive dielectric and the analyte;

a second electrode with a second ion-sensitive dielectric provided thereon, the second electrode being arranged for contacting the analyte via the second ion-sensitive dielectric to obtain a second interface between the second ion-sensitive dielectric and the analyte, and a control means for measuring a potential difference between the first electrode and the second electrode at least two different values of a temperature difference between the first interface and the second interface to obtain at least two measurement points of a surface-potential versus interface-temperature curve.

The effect of the features of the electrochemical sensor in accordance with the invention can be understood as follows. In electrochemical sensors, the reactions of interest occur at the surface of the measurement electrode. It is of interest to control the potential drop across the interface between the surface of the measurement electrode and the solution (i.e., the surface potential). However, it is impossible to control or measure this surface potential without placing another electrode in the solution. Thus, two potentials must be considered, neither of which can be measured independently. The reason why in the electrochemical sensors known from the prior art the reference electrode must produce a fairly accurate reference voltage is that otherwise the charged particle concentration cannot be determined from the Nernst equation, i.e. the absolute value of the surface-potential must be known.

The inventors have realized that the charged particle concentration may also be determined in a different manner, namely it may be determined from the surface-potential versus temperature curve, and in particular from the slope of this curve. In order to do so the electrochemical sensor comprises a first electrode with a first ion-sensitive dielectric provided thereon. The first electrode is arranged for contacting the analyte via the first ion-sensitive dielectric to obtain a first interface between the first ion-sensitive dielectric and the analyte. The electrochemical sensor further comprises a second electrode with a second ion-sensitive dielectric provided thereon. The second electrode is arranged for contacting the analyte via the second ion-sensitive dielectric to obtain a second interface between the second ion-sensitive dielectric and the analyte. The electrochemical sensor further comprises a control means for measuring a potential difference between the first electrode and the second electrode at least two different values of a temperature difference between the first interface and the second interface to obtain at least two measurement points of a surface-potential versus interface-temperature curve.

The electrochemical sensor enables determination of the charged particle concentration in the analyte as follows. First, the control means ensures that the temperature difference of the interface between the first electrode and the analyte reaches a first value. Subsequently, the first electrode and the second electrode can be "read-out" to give the potential difference corresponding with the first temperature difference. These two steps are subsequently repeated for at least a second temperature difference, wherein the second temperature difference differs from the first temperature difference. This gives a total of at least two measurement points of a surface-potential versus temperature curve and which enables to determine a corresponding slope. Once the slope has been determined, the corresponding charged-particle concentration can be calculated from the slope.

The absolute values of the corresponding potential of the at least two measurement points in said curve are dependent on the absolute potential of the analyte as defined by a reference electrode. However, in the electrochemical sensor in accordance with the invention it is not required that the reference potential is known or accurately determined, nor that it does not vary with the charged particle concentration, because the charged particle concentration is determined by the slope of said curve. Moreover, in the electrochemical sensor in accordance with the invention it is even not required to set a DC-potential of the analyte with the reference electrode. In the prior art solutions, the setting of the DC-potential of the analyte with the reference electrode closes the measurement "loop" and thereby defines the DC-potential difference between the reference electrode and the measurement electrode. In the electrochemical sensor in accordance with the invention it is sufficient to close the measurement signal-path using a capacitor. In operational use this signal path comprises:

a first capacitance defined by the first electrode, the first ion-sensitive dielectric, and the analyte;

a second capacitance defined by the second electrode, the second ion-sensitive dielectric, and the analyte;

a resistance defined by the analyte between the respective ion-sensitive dielectrics of the first and second electrode, and an input impedance of a voltage- or current-measurement device connected between the first electrode and the second electrode for measuring the potential difference.

The inventors have realized that the signal-path is closed with a second electrode with a second first-ion-sensitive dielectric which forms a capacitance together with the analyte. In the invention this is sufficient, because the potential difference is modified by the temperature and thus generates a transient voltage. For measurement of transient voltages there is no need to establish a closed DC-loop. A reference electrode (with or without reference electrolyte) to set a DC-potential of the analyte, is no longer required.

In an embodiment of the sensor in accordance with the invention the control means comprises a temperature setting means arranged for setting the temperature difference between the first interface and the second interface to said at least two different values. Providing such temperature setting means is a first way of enabling to measure the potential difference at least two different temperatures between the measurement electrode and the analyte to obtain at least two measurement points of said curve.

In an embodiment of the sensor in accordance with the invention the temperature setting means comprises a device for heating and/or cooling, the device being arranged for setting a temperature of the first interface. This embodiment advantageously provides a temperature difference between the first interface and the second interface. Such temperature setting may be done by heating and/or by cooling. This embodiment also features keeping the temperature of the second interface constant, which turns the second electrode in some sort of reference capacitance (capacitive reference).

In an embodiment of the sensor in accordance with the invention the temperature setting means comprises a resistive heater wherein the temperature is set by controlling a current through the heater. The advantage of the sensor in accordance with the invention is that the absolute value of the temperatures at which the surface-potential is measured need not be known. For obtaining slope information in said curve, it is only required to know the temperature shift. This embodiment is particularly advantageous because, in an environment, having a certain temperature and a constant heat loss, i.e. an environment in thermal equilibrium, each respective current value (or current duty cycle in case of pulsed current) through the resistive heater will correspond with a predetermined steady-state temperature of the analyte at the interface. Expressed differently, the current controls the interface temperature shift with respect to the environmental temperature, which gives the required information for determining the charged particle concentration. No additional temperature sensor for determining the absolute interface temperature is required.

In an embodiment of the sensor in accordance with the invention the temperature sensor further comprises means for determining the power dissipation of the resistive heater and thereby determining the temperature of the interface between the measurement electrode and the analyte.

In an embodiment of the sensor in accordance with the invention the temperature setting means comprises a further device for heating and/or cooling, the device being arranged for setting a temperature of the second interface. The embodiment feature separate control of the temperature of the interfaces, and thereby more precisely and easily controls the temperature difference. Also, the temperature may settle faster, thus improving the measurement speed.

In an embodiment of the sensor in accordance with the invention a semiconductor layer is provided between the first electrode and the first ion-sensitive dielectric. The semiconductor layer turns the structure into an electrolyte semiconductor insulator (EIS) structure. This embodiment of the sensor constitutes a relative simple but very effective EIS-based sensor for carrying out the charged particle measurement in accordance with the invention. This embodiment of the sensor can be easily integrated in a semiconductor device. The fact that this sensor does not need a reference electrode further improves the miniaturization of the sensor. In EIS-based sensors the flat-band voltage of the EIS capacitor yields information on the pH/ion concentration of the electrolyte. It is determined by C-V (capacitance-voltage) measurements or with a constant-capacitance method. Both methods require an electrode to modulate the analyte potential for the capacitance measurements. The inventors have realized that in the invention this analyte potential modulation can be done by the second electrode (capacitive reference) as explained later in the description. Again the temperature at the dielectric/electrolyte interface is modulated with a heater underneath the EIS layer stack. Temperature changes affect the surface potential causing a shift in the flat-band voltage. Thus the surface potential is indirectly measured via the flat-band voltage An embodiment of the sensor in accordance with the invention further comprises a transducer for measuring said potential difference. An integrated transducer not only features measurement of the potential difference, it also effectively closes the signal path.

In an embodiment of the sensor in accordance with the invention the transducer comprises a differential amplifier connected with its inputs to said first electrode and said second electrode or a transistor connected with its gate to said first electrode and with its source to the second electrode. Both transducer types can be easily integrated in a semiconductor device. When a transistor is used as transducer, such transistor forms a so-called extended-gate field-effect-transistor (EGFET) together with the first electrode. In case of a transistor as transducer the source thereof (and thus the second electrode too) may be connected to a common ground for example.

In an embodiment of the sensor in accordance with the invention a switching element with an input, an output, and a control gate, wherein the switching element arranged for receiving a DC-bias voltage on the input and being connected with the output to the first electrode the switching element is controlled by a control signal and arranged for temporarily transferring the DC-bias-voltage from its input to the first electrode before a measurement is carried out. In particular, when a transistor is used as transducer, it may be preferred to preset the gate voltage of that transistor in accordance with this embodiment. It must be noted that the DC-potential of the transistor is otherwise not properly defined, nor is the operation point of the transistor. Pre-setting is preferably done just before doing a measurement, because charge may leak away from the gate which affects the operating point of the transducer.

An embodiment of the sensor in accordance with the invention comprises a further switching element with a further input, a further output, and a further control gate, wherein the further switching element is arranged for receiving a further DC-bias voltage on the further input and being connected with the further output to the second electrode, and wherein the further switching element is controlled by a further control signal and arranged for temporarily transferring the further DC-bias-voltage from its input to the second electrode before a measurement is carried out. This embodiment where both electrodes are set follows the same advantage as the previous embodiment. In particular this is useful in case of a differential amplifier (connected to both electrodes) as transducer.

In an embodiment of the sensor in accordance with the invention the control means comprises a controller, the controller being coupled to the first electrode and being arranged for initiating the measuring of the potential difference between the first electrode and the second electrode at said at least two different values to obtain at least two measurement points of a surface-potential versus interface-temperature curve. Providing such controller, is a second way of enabling to measure the surface-potential at least two different temperatures of the interface between the measurement electrode and the analyte to obtain at least two measurement points of said curve. This embodiment is advantageous in case the temperature of the analyte is not constant over time, i.e. because of external influences. All what is required in that situation, is that the controller initiates the measurement of the surface-potential at two different temperature values measured by the temperature sensor.

In an embodiment of the sensor in accordance with the invention the controller comprises a temperature sensor for measuring the at least two different values of the temperature difference, wherein the controller is further arranged for initiating the measuring of the surface-potential at a desired value of the temperature difference. This embodiment of the invention features a better control of the respective temperatures of the interfaces and thereby a better control of the temperature difference.

In an embodiment of the sensor in accordance with the invention the controller comprises storage means for storing the respective measured values of the surface-potential and, optionally, the respective values of the temperature difference between the first interface and the second interface. Surface-potentials (optionally together with the respective temperature or temperature change) that have been stored in the storage means, can be read-out at any time in order to enable calculation of the charged particle concentration.

In an embodiment of the sensor in accordance with the invention the controller comprises a processor unit for calculating the charged particle concentration from the at least two measurement points of said curve. This embodiment conveniently provides the charged particle concentration when the measurement has been carried out. There is no need to do this manually anymore. The processor unit may be under software control or it may be a universal piece of hardware such as a gate array.

In an embodiment of the sensor in accordance with the invention at least the first ion-sensitive dielectric is further provided with a probe molecule layer comprising probe molecules, such as i) antibodies, and ii) DNA/RNA strands, the probe molecule layer being in direct contact with the analyte in operational use, the first ion-sensitive dielectric thereby being configured for binding charged target molecules for enabling to determine a charged target molecule concentration in the analyte. This embodiment of the sensor constitutes a molecule sensor, which makes use of the same principle as the other embodiments in accordance with the invention (measurement at two different temperatures). Such biosensor has a wide application area. In a variation on this embodiment the probe molecules are directly provided on the first electrode. In that embodiment the first ion-sensitive dielectric is not required.

In an embodiment of the sensor in accordance with the invention the charged target molecules are charged biomolecules.

There are various application areas for molecule or biosensors, for example: drug discovery, DNA sequencing, disease detection at the hospital/doctor (point of care), tumor marking, home use (e.g. glucose), security (biological warfare agents), and forensic research. Corresponding biomolecules that may be of interest in these areas are: drugs, DNA, viruses and pathogens, tumor markers, glucose, antibodies, etc.

In an embodiment of the sensor in accordance with the invention the sensor is arranged for determining a hydrogen ion concentration and thereby a pH-value of the analyte.

In a second aspect, the invention relates to a semiconductor device comprising an electrochemical sensor in accordance with the invention, wherein the semiconductor device comprises a semiconductor body and at least one interconnect layer, wherein the first electrode and the second electrode are located in the at least one interconnect layer, and wherein the control means are located in the semiconductor body and/or the at least one interconnect layer. It is a great advantage of the invention that the electrochemical sensor can be integrated into a semiconductor device. All mentioned features in the embodiments can be integrated onto the same semiconductor device, including the temperature setting means, the control means, the controller, the temperature settings means, the temperature sensor, data processing means, memory, etc.

In a third aspect, the invention relates to an RFID-tag comprising an electrochemical sensor in accordance with the invention. The invention is advantageously applied in this application area.

In a fourth aspect, the invention relates to a method of determining a charged particle concentration in an analyte, the method comprising steps of:
  determining at least two measurement points of a surface-potential versus interface-temperature curve, wherein the interface temperature is obtained from a temperature difference between a first interface between a first ion-sensitive dielectric and the analyte and a second interface between a second ion-sensitive dielectric and the analyte, and wherein the surface-potential is obtained from a potential difference between a first electrode and a second electrode onto which said first ion-sensitive dielectric and said second ion-sensitive dielectric are respectively provided, and
  calculating the charged particle concentration from locations of the at least two measurement points of said curve.

The advantages and effects of the method in accordance with the invention follow that of corresponding embodiments of the electrochemical sensor. The inventors have realized that the particle concentration information is hidden in the slope of the surface-potential versus interface-temperature curve. A vertical shift of said curve does not have any influence on the slope. Thus any constant potential offset caused by an undefined DC potential of the analyte does not have an effect on the measured slope and consequently the determined charged particle concentration. As explained earlier for the sensor, two electrodes having a similar configuration can be used. There is no more a need for a reference electrode. Nevertheless, it is still possible to add a reference electrode in order to define the DC potential of the analyte. Such an embodiment is advantageous in case the DC-potential of the analyte tends to change during the measurement itself, i.e. between the measurements of the surface potential at least two different temperatures.

In an embodiment of the method in accordance with the invention the step of calculating the charged particle concentration comprises the following sub-steps: i) deriving the slope from the at least two measurement points, and ii) calculating the charged particle concentration in the analyte from the slope.

In an embodiment of the method in accordance with the invention, in the step of determining, at least three measurement points of said curve are determined, and wherein the step of calculating the charged particle concentration comprises the following sub-steps: i) determining a straight fitting line using the at least three measurement points of said curve, and ii) calculating the charged particle concentration from the straight fitting line. The advantage of this embodiment of the method is that measurement noise and measurement errors are reduced.

In an embodiment of the method in accordance with the invention the sub-step of calculating the charged particle concentration comprises: a) determining a slope of the straight fitting line, and b) calculating the charged-particle concentration from the slope.

In an embodiment of the method in accordance with the invention the step of determining of said curve comprises sub-steps of:
  setting the temperature difference to a first value;
  determining a first value of the potential difference, wherein the first value of the temperature difference and the first value of the potential difference together define a first respective one of the measurement points of said curve;
  setting the temperature difference to a second value different from the first value, and
  determining a second value of the potential difference at the interface, wherein the second value of the temperature difference and the second value of the potential difference together define a second respective one of the at least two measurement points of said curve. This embodiment of the method constitutes a possible implementation of determining said curve.

In an embodiment of the method in accordance with the invention the difference between the first value of the temperature difference and the second value of the temperature difference is smaller than a predefined threshold, preferably smaller than or equal to 10K, and even more preferably smaller than or equal to 5K. Keeping the temperature difference between the first and second measurement within a certain threshold ensures that a measurement error, which is the result of a temperature dependency of a specific parameter of the sensor, is reduced. This applies especially in case of a dielectric sensor layer when the temperature dependence of the sensitivity parameter $\alpha$ is unknown. Keeping a small temperature range also reduces the power consumption. The pH of the analyte may itself be temperature dependent (e.g. buffers have temperature dependent buffer capacity). Thus if the pH of a solution must be known at a certain temperature the measurement process should not deviate too much from this temperature itself. One of those temperature dependent parameters is the sensitivity of the dielectric of the ISFET-based measurement electrode, which parameter is known to be temperature dependent. What is considered as an acceptable measurement error generally depends on the application. In case of a pH measurements an error of 0.1 pH is acceptable for most applications.

In an embodiment of the method in accordance with the invention the step of determining at least two measurement points of said curve is done by determining respective values of an output quantity that is indicative of the potential difference. Depending on the chosen type of transducer it may be that the output is a quantity that is representative of the surface-potential, i.e. a current through a transistor, output of differential amplifier, shift in C-V curve of an EIS device.

It is important to note that, despite the fact that a real reference electrode is no longer needed in the electrochemical sensor in accordance with the invention, a real reference electrode may still be applied in the measurement principle in accordance with the invention (i.e. determining a charged-particle concentration from the slope of a potential-versus-temperature curve).

These and other aspects of the invention are apparent from and will be elucidated with reference to the embodiments described hereinafter.

BRIEF DESCRIPTION OF THE DRAWINGS

In the drawings:

FIG. 1 shows some formula's for explaining the potentiometric measurement principle as known from the prior art;

FIG. 3 shows some formula's for explaining the potentiometric measurement principle in accordance with the invention;

DETAILED DESCRIPTION OF THE PREFERRED EMBODIMENT

Figure 2:
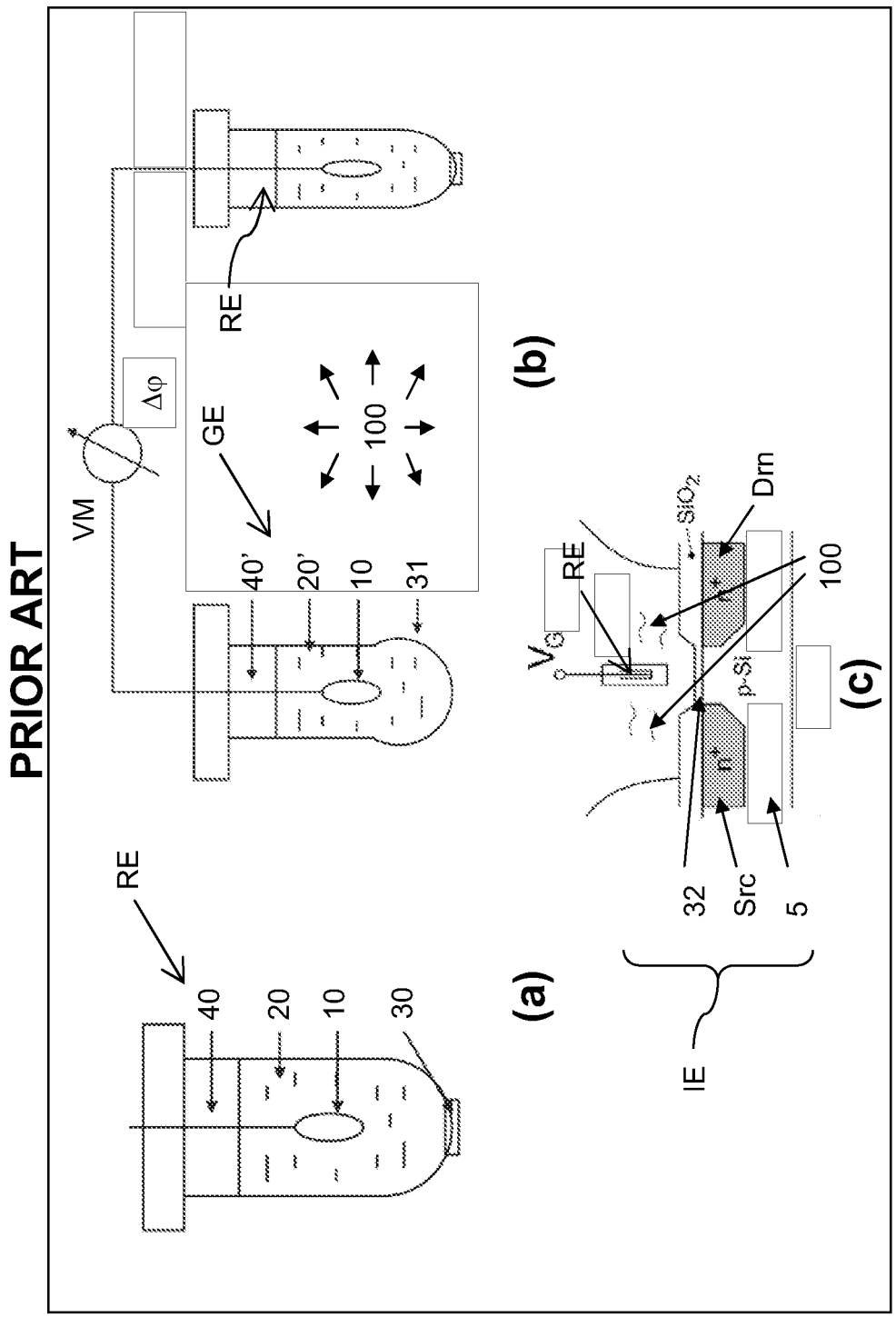
FIGS. 2(a) to 2(c) show conventional electrodes and reference electrodes known from the prior art.

The invention provides a new method for determining a charged particle, i.e. ions and charged biomolecules, concentration in a liquid analyte. In an embodiment the method concerns determination of a hydrogen ion concentration and thereby the pH-value. It is based on surface-potential measurements at different temperature differences of two electrode analyte interfaces. The electrochemical sensor comprises a first electrode (with a first ion-sensitive sensor dielectric) and a second electrode (with a second ion-sensitive dielectric). The first electrode may be part of an ISFET, an EGFET, or an EIS capacitor. The second electrode may comprise the same layers and materials as the first electrode, which is one of the key advantages over the known electrochemical sensors. The charged particle concentration is calculated from the surface-potential versus temperature curve which is obtained by determining the potential difference between the first electrode and the second electrode at least two different temperature differences between the respective electrodes. As the charged particle concentration is "hidden" in the slope of this curve, it is even not required to know the absolute temperature of each of the respective electrodes. It is only required to know the temperature difference. Because of the new measurement principle no reference electrodes in the common sense are needed any more. All problems and issues associated with these reference electrodes are thereby prevented (e.g. maintenance and refill of electrolyte, bulky device, limitations in temperature range, etc.). Moreover, the new method of measuring a charge particle concentration is a dynamic measurement type (the temperature is modulated), which minimizes drift and reduces the need for frequent calibration.

In view of the above the invention provides a method of determining a charged particle concentration, an electrochemical sensor for determining the charged particle concentration using such method, a semiconductor device comprising such electrochemical sensor, and an RF-ID tag comprising such electrochemical sensor.

In order to facilitate the discussion of the detailed embodiments a few expressions are defined hereinafter.

Throughout this description the term "interface temperature" should be interpreted as the temperature of a volume around the interface which includes volume with electrode material and a volume with analyte.

In electrochemistry, the Nernst equation is an equation which can be used (in conjunction with other information) to determine the equilibrium reduction potential of a half-cell in an electrochemical cell.

A half cell is a structure that contains a conductive electrode and a surrounding conductive electrolyte separated by a naturally-occurring Helmholtz double layer. Chemical reactions within this layer momentarily pump electric charges between the electrode and the electrolyte, resulting in a potential difference between the electrode and the electrolyte. The typical reaction involves a metal atom in the electrode being dissolved and transported as a positive ion across the double layer, causing the electrolyte to acquire a net positive charge while the electrode acquires a net negative charge. The growing potential difference creates an intense electric field within the double layer, and the potential rises in value until the field halts the net charge-pumping reactions. In a similar way the Nernst equation also describes the surface potential at the interface of a dielectric and an electrolyte or across a membrane with different ion concentrations in the electrolytes on either side.

Throughout this description the term "reference electrode" refers to an electrode which has a stable and well-known electrode potential. The high stability of the electrode potential is usually reached by employing a redox system with constant (buffered or saturated) concentrations of each participants of the redox reaction. Reference electrodes are used to build an electrochemical cell in conjunction with an electrode the potential of which is to be determined. Each electrode represents a half cell; both are required to complete the circuit and measure the unknown potential.

Throughout this description the term "pseudo-reference electrode" refers to a reference electrode which does not maintain a constant potential. By definition, a pseudo-reference electrode is not a true reference electrode. However, its potential depends on conditions in a well-defined manner; if the conditions are known, the potential can be calculated and the electrode can be used as for reference potential.

Throughout this description the term "measurement electrode" is considered either an ISFET, an EGFET or an EIS capacitor.

Throughout this description the term "charged particle" refers to ions and charged bio-molecules.

Throughout this description the term "interconnect layer" should be considered as synonym to "metallization layer" or "metal layer". Both terms are used interchangeably and have to be interpreted as the layer comprising conductors (any conducting material), the insulating layer in which the conductors are embedded, and any vias (=contacts) to underlying layers. These terms are well-known to the person skilled in the art of semiconductor technology.

Throughout this description the term "substrate" should be interpreted broadly. The substrate may comprise an active layer with elements, such as transistors and diodes, which form the components of an electronic circuit. The substrate may further comprise interconnections between the elements which may be laid out in one or more interconnect layers and may further contain passive elements such as capacitors, resistors and inductors. In the figures, the elements have been left out in order to facilitate the understanding of the invention. The active layer in which the elements are formed may also be called a semiconductor body. The semiconductor body may comprise any one of the following semiconductor materials and compositions like silicon (Si), germanium (Ge), silicon germanium (SiGe), gallium-arsenide (GaAs) and other III-V compounds like indium-phosphide (InP), cadmium sulfide (CdS) and other II-VI compounds, or combinations of these materials and compositions as well as semiconducting polymers. The active elements together may form an electronic circuit. In any case, connection of the active elements is done via interconnect layers. These interconnect layers have parasitic capacitances which are defined by the dielectric constant of surrounding materials. The semiconductor body may even comprise contacts to lower layers (e.g. diffusion regions at the surface of an active region).

FIG. 1 shows some formula's for explaining the potentiometric measurement principle as known from the prior art. In the description of the figures the main principle will be explained with measurement of a concentration of hydrogen ions (pH-value). However, it must be stressed that the invention is also applicable to any other kind of charged particle concentration, i.e., $Na^+$-ions, $K^+$-ions, $Ca^{2+}$-ions, etc.

The pH-value is an integral parameter of every (aqueous) solution. It describes to which degree the solution is alkaline or acidic. Over a wide range it is well approximated by: $pH=-\log_{10}[H^+]$, wherein $[H^+]$ denotes the proton concentration of the solution in mol/L. pH-measurement is a routine task in industry and also in laboratories for process control and analysis. However, it could also become interesting for a wider application range if the pH-measurement units (sensor plus electronics) become sufficiently inexpensive. E.g., there is a large potential for pH-measurement to monitor the quality of (liquid) perishables in the supply chain or even at the customer himself. Experimental techniques for measuring ion concentrations (as is the case in pH-measurements) can be divided into two classes, non-electrochemical methods, e.g., optical (indicator dyes), catalytic, and swelling of polymers (gels), and electrochemical methods. The latter are widely used for many applications in industry and laboratories. Electrochemical ion concentration sensors rely on the potentiometric principle, i.e. they measure the electrical potential $\phi$ across a solid/liquid interface which is a function of the ion concentration to be determined. The potential $\phi$ can be calculated from the Nernst equation, given in formula (1) of FIG. 1. In this formula k is the Boltzmann constant, T the absolute temperature in Kelvin, q the elementary charge, and n the ionic charge (e.g. n=1 for $H_3O^+$, $Na^+$; n=2 for $Ca^{2+}$). Ion concentrations at both sides of the membrane/interface (1 and 2) are represented in terms of activities $a_i=f_i*c_i$ with $f_i$ being the activity coefficient ($f_i=1$ for diluted electrolytes) and $c_i$ the respective ion concentration in mol/L. According to the Nernst equation the electrode potential is a logarithmic function of the ion activity on one side of the membrane/interface if the activity on the other side is kept constant. Depending on the type of ion described by parameter "a" the sensor is sensitive to $H_3O^+$-ions, $Na^+$-ions, $Ca^{2+}$-ions, etc.

FIGS. 2(a) to 2(c) show conventional electrodes and reference electrodes known from the prior art. All major pH-(ion)-measurement electrodes work according to the principle described above, including the well-known glass electrodes (different glass compositions sensitive to pH, pNa, pK etc. have been developed), antimony electrodes, ISFET's (Ion Sensitive Filed Effect Transistor) and EIS capacitors (Electrolyte Insulator Semiconductor capacitor; here the flat-band voltage is a function of the pH of the electrolyte). It is not possible to measure a potential; but it is possible to measure potential differences. In any case, in order to measure a potential difference with a measurement electrode a reference electrode is needed, wherein the potential difference is generated by a difference in the measurement electrode potential $\phi_m$ and the reference electrode potential $\phi_{ref}$ (see formula (2) in FIG. 1). In the case of ISFET and EIS devices as measurement electrode the reference electrode is also used to set the operating point and close the electric loop. In the prior art, the potential of the reference electrode $\phi_{ref}$ with respect to the electrolyte potential must remain constant irrespective of the analyte composition. Thus, in the prior art, what is measured is the potential difference $\Delta\phi$ between the measurement electrode potential $\phi_m$ and the reference electrode potential $\phi_{ref}$. This is given by formula (2) in FIG. 1.

In the case of a pH-measurement with a glass-electrode and a conventional reference electrode (with a reference liquid), the potential difference can be given by (3a) formula in FIG. 1. In formula (3a) pHin stands for the pH of the electrolyte in the glass-electrode and pHout stands for the pH of the analyte (which has to be determined). In fact formula (3) is the sum of two surface potentials at the inside and outside of the glass electrode as well as the contact potential of the wire inside the glass electrode with the electrolyte in the glass-electrode $\phi_{cont}$ and the reference electrode potential $\phi_{ref}$. However, in this configuration these terms cancel each other out when both electrodes have the same temperature. The derivation of formula (3a) and more information on reference electrodes can be found in the following publication:

"*Measuring, modeling, and controlling the PH-value and the dynamic chemical state.*" By Jean-Peter Ylén, Helsinki University of Technology, Control Engineering Laboratory, Report 127, Espoo 2001 [REF1]. This document has been incorporated by reference in its entirety.

In the case of a pH-measurement with an ISFET-measurement electrode and a conventional reference electrode, the potential difference can be given by (3b) formula in FIG. 1. In formula (3a) parameter "pHpzc" stands for the point of zero charge of the ISFET-measurement electrode (a material property defined by the dielectric sensor layer of the ISFET) and pHout stands for the pH of the analyte (which has to be determined). The derivation of formula (3b) and more information on ISFET electrodes can be found in the following publication:

P. Bergveld, "*Thirty years of ISFETOLOGY. What happened in the past 30 years and what may happen in the next 30*

*years."*, Sensors and Actuators B 88 (2003) 1-20 [REF2]. This document has been incorporated by reference in its entirety.

Besides the standard hydrogen electrode, the Ag/AgCl electrode is the most well-known reference electrode. This reference electrode RE is illustrated in FIG. 2(a). It consists of a chlorinated silver wire 10 (Ag/AgCl) in contact with a well-defined electrolyte 20 (often 3 mol/L KCl). Galvanic contact to the analyte is established via a diaphragm 30 (porous frit from glass or ceramics, etc.). During operation the electrolyte 20 must continuously flow out of the reference electrode RE into the analyte. Other reference electrodes, e.g. calomel electrodes (based on mercury) or Tl/TlCl electrodes are used for specific applications, e.g. at elevated temperatures. Their principle is the same as for the Ag/AgCl electrode, in particular the use of a liquid electrolyte 20 and contact via a diaphragm 30. The chlorinated silver wire 10 is connected to a contact cable 40.

FIG. 2(b) illustrates a measurement set-up in which the reference electrode RE is used in combination with a glass electrode GE. Both electrodes GE, RE are immersed into the analyte 100 in operational use. The glass electrode GE comprises a chlorinated silver wire 10 (Ag/AgCl) in contact with an electrolyte 20' (buffer solution) with a well-defined $pH_{in}$-value. The electrolyte 20' is provided in a pH-sensitive glass membrane 31, which is produced from a special glass. Its thickness is usually between 50-200 μm, but in the measurement of very aggressive solutions it can be even 1 mm. After immersion in water the glass electrode can measure the process solution 100 (analyte). A potential difference between the analyte 100 and the glass surface is created, and this difference is a function of the activity of $H_3O^+$-ions and thus also a function of the pH-value of the analyte 100. The chlorinated silver wire 10' is connected to a further contact cable 40'. The cable 40 and the further cable 40' are both connect to the input of a voltmeter VM. The voltmeter gives the potential difference $\Delta\phi$ as given by formula (3a) in FIG. 1. More information about glass electrodes can be found in the first reference (REF1) given in this description.

FIG. 2(c) illustrates a measurement set-up in which the reference electrode RE is used in combination with an ISFET measurement electrode IE. Both electrodes IE, RE are immersed into the analyte in operational use. The ISFET measurement electrode IE comprises a transistor structure, which is very similar to a conventional field-effect transistor (FET). It comprises a p-type substrate 5 having an n-type source Src and an n-type drain Drn provided at a surface thereof defining a channel region in between. A gate dielectric 32 is provided on the substrate 5 covering source Src, drain Drn and channel. Alternative a p-type transistor can be used. A main difference with respect to a conventional MOSFET is that the gate dielectric 32 is in direct contact with the analyte 100 instead of with a poly/metal gate contact. The gate dielectric 32 is the ion/pH sensitive layer (in an example embodiment it comprises $SiO_2$, but other dielectrics, such as $Ta_2O_5$ can also be used). The transistor acts as transducer that converts the potential difference into a current between the source Src and drain Drn of the transistor. Above the channel region the dielectric may be thinner than elsewhere, in order to increase the sensitivity of the ISFET (better control of the channel in case of a predefined surface potential generation at the dielectric layer 32). More information about ISFET's can be found in the second reference (REF2) given in this description. A reference electrode RE is provided in the analyte 100 in order to establish a "working point" (reference potential) for the ISFET and define the analyte potential. A potential set by this reference electrode RE may be considered as the gate voltage $V_G$ of a conventional field-effect transistor. In the prior art pH-measurements it is of utmost importance that the potential of the reference electrode is independent of the composition of the analyte.

Figure 8:
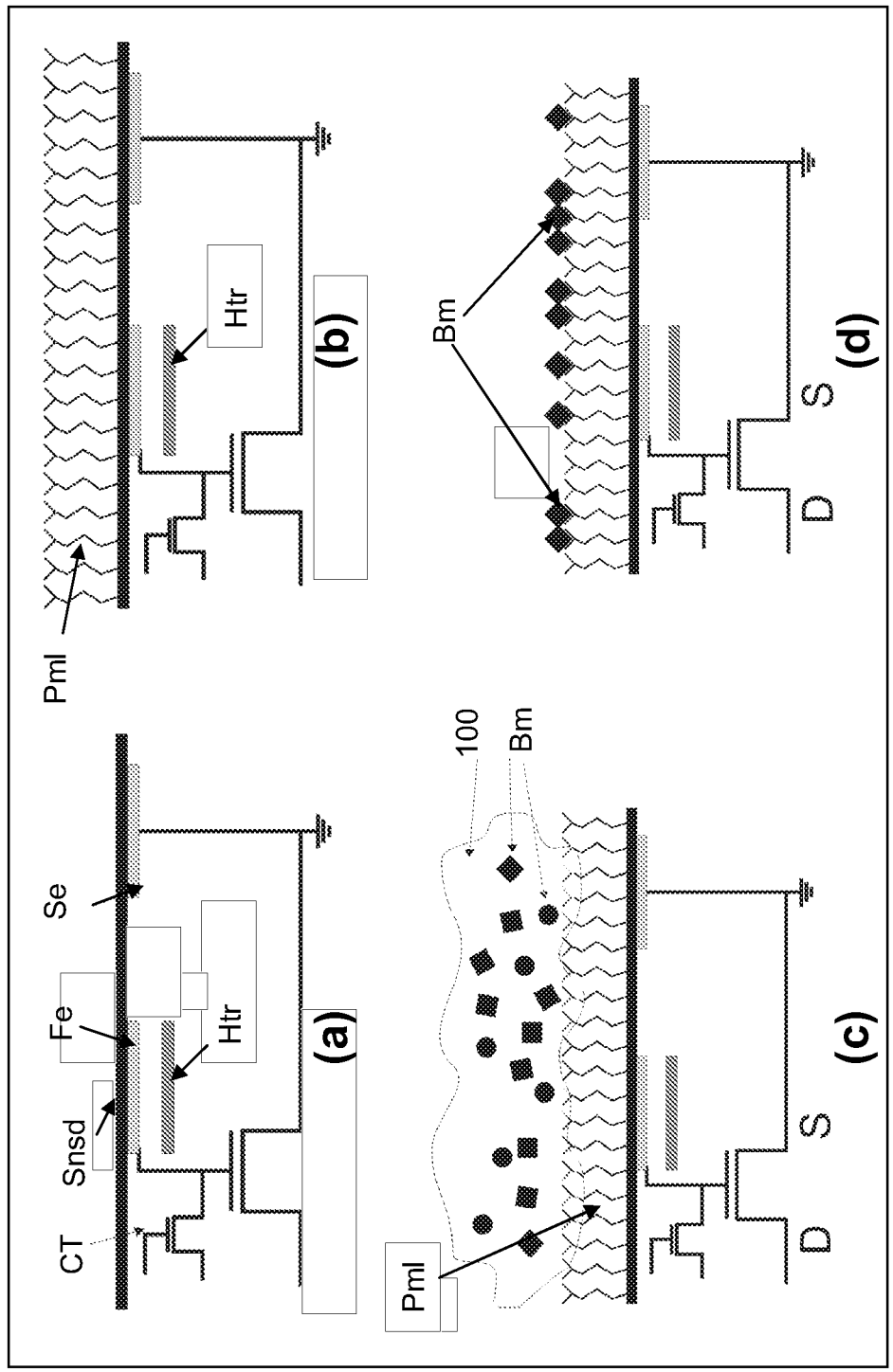
FIGS. 8(a) to 8(d) show the manufacturing and operation principle of an electrochemical biosensor in accordance with yet another embodiment of the invention.

FIG. 3 shows some formula's for explaining the potentiometric measurement principle in accordance with the invention. An essential feature of the invention is to execute potentiometric pH/ion measurements at different temperatures in the (same) analyte. While temperature changes must be compensated or taken into account with the conventional potentiometric measurement principle of the prior art the invention exploits the temperature dependency of the sensor output to determine the quantity to be measured, e.g., the pH-value or ion concentration of a solution (or a charged biomolecule concentration as will be discussed in FIG. 8). The arguments described hereafter relate to pH-value but also apply to ion concentration or charged biomolecule concentration, then the pH needs to be replaced by pK and the charge number n must be taken into account).

The potential difference equation for a combination of a glass electrode and a conventional reference electrode (with reference liquid) is repeated in formula (4a) in FIG. 3, wherein pHout denotes the pH-value at the outside (analyte) and pHin denotes the pH-value of the electrolyte inside (ln 10≈2.3). The inventors have realized that formula (4a) can be looked at differently. According to this formula $\Delta\phi$ shows a linear dependence on T with the slope of the straight line m given by formula (4b) in FIG. 3. It must be noted that all parameters of this formula are known or fixed, except for pHout which is the pH-value of the analyte to be measured. Following this approach the pH-value of an analyte can be obtained by recording the potential difference $\Delta\phi$ at different temperature differences, determining the slope m of the $\Delta\phi$-T curve and subsequently calculating the pH-value using formula (4c) in FIG. 3. Alternatively, it is also possible to determine the slope by varying the temperature of two electrode-analyte interfaces in a different way in order to create said temperature differences (instead of only setting a temperature of the first interface). The surface potential difference $\Delta\phi$ can then be determined by determining the potential difference between said two electrodes.

Figure 4:
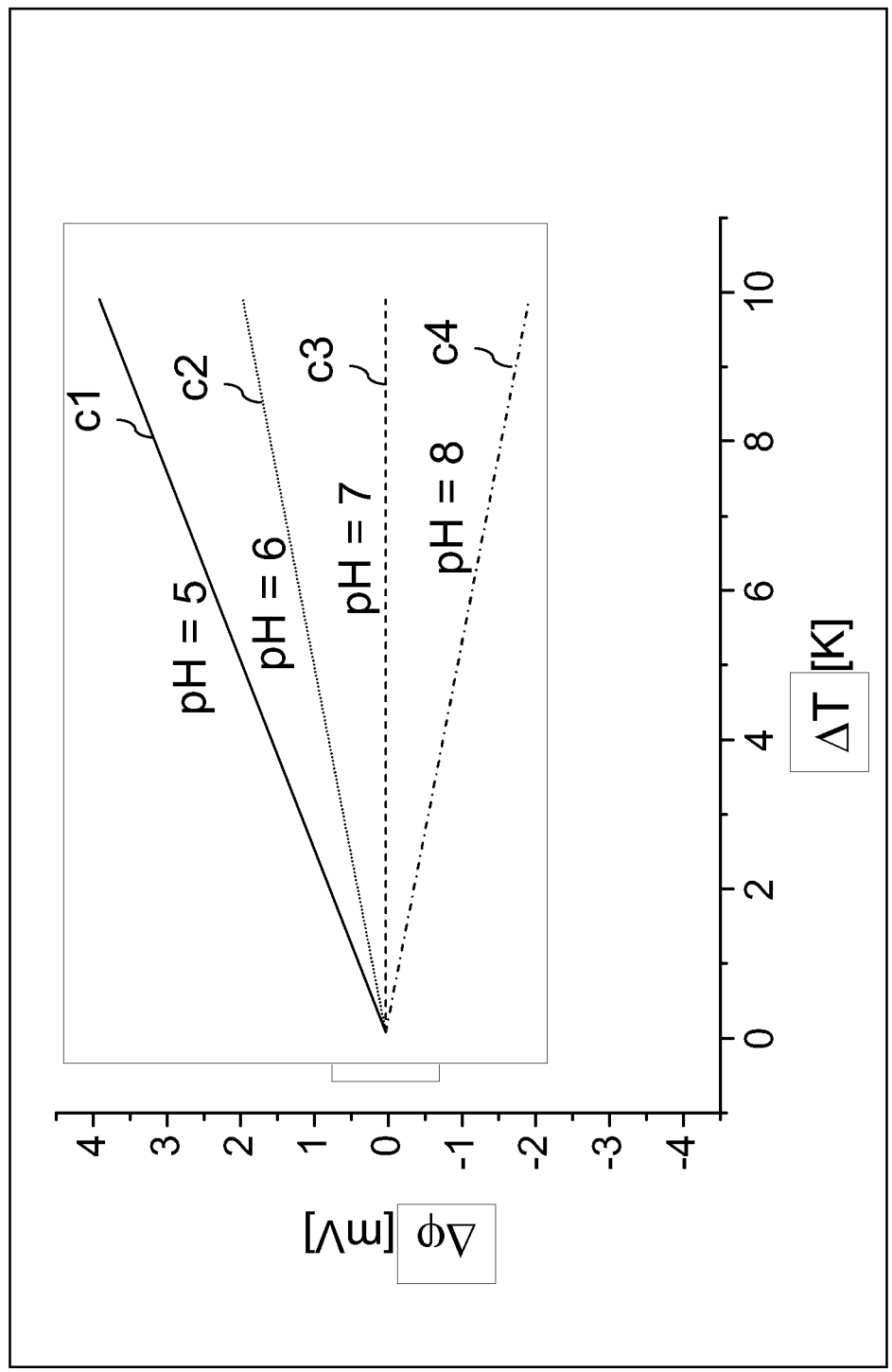
FIG. 4 shows a diagram with a couple of potential difference versus interface-temperature change curves for different charged particle concentrations.

FIG. 4 shows a diagram with a couple of potential difference (between measurement electrode and reference electrode) versus interface-temperature change curves for different charged particle concentrations. The diagram shows $\Delta\phi$-$\Delta$T-curves for various pHout-values in a temperature range 0K-10K (pHin=7). These curves have a direct relation with the surface-potential versus interface-temperature curves. The slopes of the curves allow a clear discrimination of the different pH-values. Four curves c1, c2, c3, c4 illustrate a pH-value equal to 5, 6, 7, and 8, respectively. Which curve runs horizontal depends on the value of parameter "pHin". In principle parameter "pHout" can be calculated without calibrating the sensor since all parameters in formula (4a) in FIG. 3 are known. In reality calibration may still be advisory because of components of the system that do not behave ideally and may be temperature dependent (e.g. electrode contacting the reference electrolyte inside a glass electrode with pHin).

Since the information about the pH-value (hydrogen-ion concentration) is conveyed in the slope of the $\Delta\phi$-$\Delta$T-curves rather than in the absolute value of $\phi$ (as is the case with conventional potentiometric measurements) any vertical shift of the curves has no effect on the measurement. Thus any potential offset caused by using a non-accurate reference electrode or a pseudo-reference electrode does not influence the measurement. A pseudo-reference electrode consists of a simple metal wire (e.g. Pt or Ag/AgCl) immersed in the analyte (sample solution). A pseudo-reference electrode provides a constant reference potential, but this is usually unknown and depends on the analyte composition (e.g. its ion concentration).

In the electrochemical sensor in accordance with the invention no reference electrode is required at all. Even a pseudo reference electrode is no longer required. Instead, a first electrode and the second (similar) electrode may be used, which together with the analyte and a measurement device close the electrical circuit and the respective (transient) temperatures of the respective electrode-analyte interfaces, cause a (transient) potential difference between the electrodes. For a precise measurement at a specific temperature it must only be made sure that the potential of the respective electrodes remains constant during the measurement itself, i.e. during recording of the respective $\phi$-values.

For the method it is not even necessary to know the absolute temperature of said interfaces. The only value which must be known (in arbitrary units) is the change in the temperature difference between said interfaces over the different measurements. For example, in a situation where only the first interface is heated, the temperature T for the first interface can be given as: $T=T_0+a*U_2/R*t$, wherein parameter "$T_0$" denotes the temperature at t=0 s, parameter "R" denotes the ohmic resistance of a resistive heater, parameter "U" denotes the applied voltage and parameter "t" denotes the time the heater is activated. Parameter "a" comprises all other system parameters e.g. the volume of the heated liquid and its heat capacity. Substituting this formula for the temperature with formula (4a) in FIG. 3, gives a formula for the potential difference $\Delta\phi$ as a function of time t. The absolute value of the start temperature $T_0$ does not need to be known, since it only causes a vertical shift of the curve, whereas the pH-value (pHout) is conveyed in the slope. A calibration of the system (i.e. measure the slope of a curve with a buffer of defined pHout) may be necessary in order to determine parameter "a". Moreover, parameter "a" should preferably remain constant between calibration and real measurement since it directly affects the slope. Also, it must be noted that the temperature difference between the first interface and the second interface follows directly from the temperature formula as the second interface is not heated in this example (no temperature change).

Potentiometric measurements as known from the prior art are static measurements, which rely on the thermodynamic equilibrium. Static measurements are often subject to temperature drift which makes frequent calibration necessary. Besides the associated effort and cost, some systems are difficult to calibrate, e.g. because the sensor is fixed in a vessel/pipe and would need to be removed or because the system cannot be accessed at all (perishable monitoring, medical applications). Drift is a particular problem for ISFET sensors. Various algorithms and procedures have been developed to predict drift and correct the measurements (see [REF2]) Moreover, new sensors must equilibrate for a certain time before they can be used. An advantage of the measurement principle of the invention is that due to the dynamic measurement principle drift is considerably reduced with our invention increasing the calibration intervals and measurement accuracy. More information on drift and counter-measures can be found in the following publication:

S. Jamsab, "*An Analytical Technique for Counteracting drift in Ion-Selective Field effect Transistors (ISFETs)*", IEEE Sensors J., 4 (6), 795-801, 2004 [REF3]. This document has been incorporated by reference in its entirety.

Another advantage of the new measurement principle in accordance with the invention is the noise reduction. If the slope of a $\Delta\phi$-$\Delta T$-curve is determined by fitting a straight line to several $\phi$ values recorded at different temperatures, noise and statistical measurement errors are averaged out.

Until now, for the sake of clarity only the fundamental principles and equations have been shown and discussed. In real applications it might be slightly more complex. This also depends on the type of measurement electrode and reference electrodes chosen.

In the case of a pH-measurement with an ISFET-measurement electrode and a reference electrode, the potential difference can be given by formula (5a) in FIG. 3 wherein the first part describes the surface potential (which yields the information on the pH-value of the analyte) of the dielectric/analyte interface, wherein parameter pHpzc denotes the point-of-zero-charge, i.e. the pH-value of the analyte for which the oxide surface is electrically neutral, wherein parameter pHout denotes the actual pH-value of the analyte in contact with the dielectric, wherein parameter "$\alpha$" denotes a temperature dependent sensitivity parameter which is characteristic for the specific ISFET sensor dielectric. Parameter "$\alpha$" lies between 0 and 1 (in case of a sensitivity equal to 1 the sensor has the maximum sensitivity). Formula's (5b) and (5c) can be derived from formula (5a) in a way that is similar to that of formula's (4b) and (4c) in FIG. 3.

Parameter "$\alpha$" for an ISFET is known to be defined as given in formula (6) in FIG. 3, wherein parameter $C_S$ denotes the double layer capacitance (which depends on the ion concentration in the analyte), and wherein parameter $\beta_S$ denotes the surface buffer capacity which is a material parameter of the sensor dielectric. Other parameters are already explained earlier in the description.

The temperature dependency of the sensor sensitivity a may complicate the measurement method a bit. It can be addressed in several ways (or combinations thereof).

1) Use a sensor dielectric material with high surface buffer capacity $\beta_S$. This measure minimizes the temperature dependence of the sensitivity $\alpha$. The advantage of this approach is that the measurement principle described above can applied without modification. In a preferred embodiment the sensor dielectric material comprises tantalum oxide ($Ta_2O_5$) which has the advantage that it has a very high $\beta_S$.

2) Perform the different temperature measurements in a small temperature "window", e.g. 5K. Within this temperature window the sensitivity $\alpha$ may be assumed to be constant. Consequently, a small change in the sensitivity $\alpha$ results in a relatively small error and can be neglected. This second approach requires that the calibration and "real" measurement to be made are done at the same temperature. Otherwise the error will increase because of the earlier mentioned temperature dependency, which thus results in different slopes.

3) Determine $C_S$ and $\beta_S$ during sensor calibration. A single calibration run with one reference solution is sufficient. However, the surface potential $\phi$ must be measured for several temperatures to allow fitting of the earlier described T(t) curve (of the resistive heater) to the $\Delta\phi$-T-curve in order to obtain $C_S$ and $\beta_S$. This is the most accurate approach but the absolute temperature must be known. A temperature sensor for determining the absolute temperature is thus required.

The inventors have realized that it is possible to do a pH-measurement with two measurement electrodes. In such measurement set-up the potential difference can be given by formula (7a) in FIG. 3 wherein the first part describes the surface potential (which yields the information on the pH-value of the analyte) of the first dielectric/analyte interface, wherein parameter pHpzc$_{fe}$ denotes the point-of-zero-charge of the first electrode. Parameter $T_{fe}$ denotes the temperature of the first interface. Parameter pHout denotes the actual pH-value of the analyte in contact with the first dielectric. Parameter "$\alpha_{fe}$" denotes a temperature dependent sensitivity parameter of the first measurement electrode which is characteristic for the specific sensor dielectric. The second part of formula (7a) describes the surface potential (which yields the information on the pH-value of the analyte) of the second dielectric/analyte interface, wherein parameter $pHpzc_{se}$ denotes the point-of-zero-charge of the second electrode. Parameter $T_{se}$ denotes the temperature of the second interface. Like for the first part of the formula, parameter pHout denotes the actual pH-value of the analyte in contact with the second dielectric. Parameter "$\alpha_{se}$" denotes a temperature dependent sensitivity parameter of the second measurement electrode which is characteristic for the specific sensor dielectric. When the parameters of the first electrode and the second electrode are identical (which is automatically the case if they are of the same kind and have the same structure, materials, and dimensions) formula (7a) can be rewritten into formula (7b), which clearly illustrates the linear dependency of the potential difference $\Delta\phi$ on the temperature difference $\Delta T$.

The method for measuring pH or ion concentrations can be realized in different ways. In any case a first and a second electrode (each having an ion-sensitive sensor dielectric) are required. In operational use, the first electrode forms a first interface with the analyte and the second electrode forms a second interface with the analyte. At least one of the electrodes must be provided with a small heater/cooler. This heater configuration enables to create a (variable) temperature difference between respective interfaces with the analyte. The heater/cooler heats/cools the analyte in close proximity to the first interface. The sensor readings (representing $\phi$) at different temperature differences (the temperature (difference) may be measured with an integrated sensor or determined from heating energy) are stored or plotted. This provides measurement points of a surface-potential versus temperature curve. Subsequently, the charged particle concentration may be obtained from the slope of said curve according to the method described above. Instead of a close-by heater/cooler the analyte temperature can also be controlled by a remote device and applied to the sensor by a fluidic system (e.g. flush liquid onto sensor).

If no temperature sensor is used in the method, sufficient time must pass between subsequent heat pulses to allow cooling of the sensor to the initial (ambient) temperature. If only short heat pulses are used a heat wave will propagate towards the dielectric/analyte interface leading to a transient temperature increase. Continuous measurement of the potential difference (transducer output) will result in a maximum value, which value shall be used for further data extraction (when this value is reached the temperature at the interface is highest before it cools off again). To increase measurement accuracy a curve can be fitted to determine the extreme value (taking into account the temporal behavior of the temperature at the interface following a heat pulse). A simpler way is to average a few values in an interval around the extreme value.

Where in this specification the wording "obtaining of measurement points of a surface-potential versus temperature curve" is used, it is often meant that measurement points of a potential-difference (between the first electrode and the second electrode) versus temperature difference (between the first electrode and the second electrode) is meant. Nevertheless, as in the invention it is not required to know the absolute temperature, but only to determine the slope of the surface-potential versus temperature curve, the latter curve has a clear relation with the first curve and is sufficient to obtain the slope.

So far, the description of the figures mainly dealt with the method of determining a charged particle concentration in an analyte in accordance with the invention. However, the invention also relates to an electrochemical sensor, which can be used to carry out this method. It has already been discussed that such electrochemical sensor may comprise measurement electrodes, such as ISFET's, EGFET's, and EIS capacitors. In any case the electrochemical sensor in accordance with the invention comprises a first electrode with a first ion-sensitive dielectric provided thereon, wherein the first electrode is arranged for contacting the analyte via the first ion-sensitive dielectric to obtain a first interface between the first ion-sensitive dielectric and the analyte. The electrochemical sensor further comprises a second electrode with a second ion-sensitive dielectric provided thereon, wherein the second electrode is arranged for contacting the analyte via the second ion-sensitive dielectric to obtain a second interface between the second ion-sensitive dielectric and the analyte. Further the electrochemical sensor in accordance with the invention also comprises at least a control means for measuring a potential difference between the first electrode and the second electrode at least two different values of a temperature difference between the first interface and the second interface to obtain at least two measurement points of a surface-potential versus interface-temperature curve. Such control means can be a temperature setting means arranged for setting a temperature difference between the first interface and the second interface to at least two different values. Alternatively, such control means can be a controller, wherein the controller is coupled to the first electrode and is arranged for initiating the measuring of the potential difference between the first electrode and the second electrode at said at least two different values to obtain at least two measurement points of a surface-potential versus interface-temperature curve. A combination of both is also possible.

Miniaturized solutions for the electrochemical sensor are of particular interest as that opens up new application possibilities. An example of such miniaturization is the ISFET measurement electrode. A disadvantage of the ISFET is that with the measurement principle of the prior art still an accurate reference electrode (with reference electrolyte) is required, which electrode cannot be easily miniaturized. Miniaturized versions, which have been reported in the prior art so far, have a very limited life-time.

A major advantage of the invention is that this cumbersome reference electrode is no longer required. Even a pseudo-reference electrode (which is basically a piece of wire immersed in the analyte in operational use) is no longer required. Instead a second electrode, similar to the first electrode is provided, which can be easily integrated into the same device as the first electrode. Miniaturization has thus become very easy. Nevertheless, it is still possible to combine the electrochemical sensor of the invention with a conventional reference electrode or a pseudo-reference electrode. As already mentioned such additional reference electrode allows setting a DC-potential of the analyte, which is advantageous in case the floating potential of the analyte tends to drift during a measurement.

The main building blocks of an electrochemical sensor in accordance with an embodiment of the invention are:
 a first electrode covered with a suitable sensor material (depending on the application pH or ion sensitive);
 a second electrode covered with a suitable sensor material (depending on the application pH or ion sensitive);

a heater/cooler in close proximity to at least the first electrode, and a transducer for transducing the sensor output (potential difference between first and second electrode) into an electrical signal for further processing.

Moreover, the electrochemical sensor may include circuits for data processing and storage, power supply. The electrochemical sensor may further comprise circuit blocks, such as AD/DA converters, digital signal processors, memory and RF units for wireless data transfer.

FIGS. 5(a) to 5(d) show four embodiments of the electrochemical sensor in accordance with an embodiment of the invention. FIG. 5(a) shows a so-called Extended Gate Field-Effect-Transistor (EGFET). It comprises a conventional transistor NM having a source Src, a drain Drn, and a gate Gt, i.e. an NMOS transistor. The gate Gt of the transistor NM is connected to a first electrode Fe via standard metal interconnect 'wires'. On the first electrode Fe a first sensor dielectric Fsd is provided that is sensitive to certain ions. The sensor has been exemplified in a simplified way to facilitate understanding of the invention. The electrochemical sensor further comprises a second electrode Se. On the second electrode Se a second sensor dielectric Ssd is provided that is sensitive to certain ions (preferably the same ions). In order to form a capacitance, the second electrode Se is arranged to contact the analyte only through the second ion-sensitive dielectric Ssd, in operational use. In operational use, the first ion-sensitive dielectric Fsd forms a first interface with the analyte and the second ion-sensitive dielectric Ssd forms a second interface with the analyte.

Figure 7:
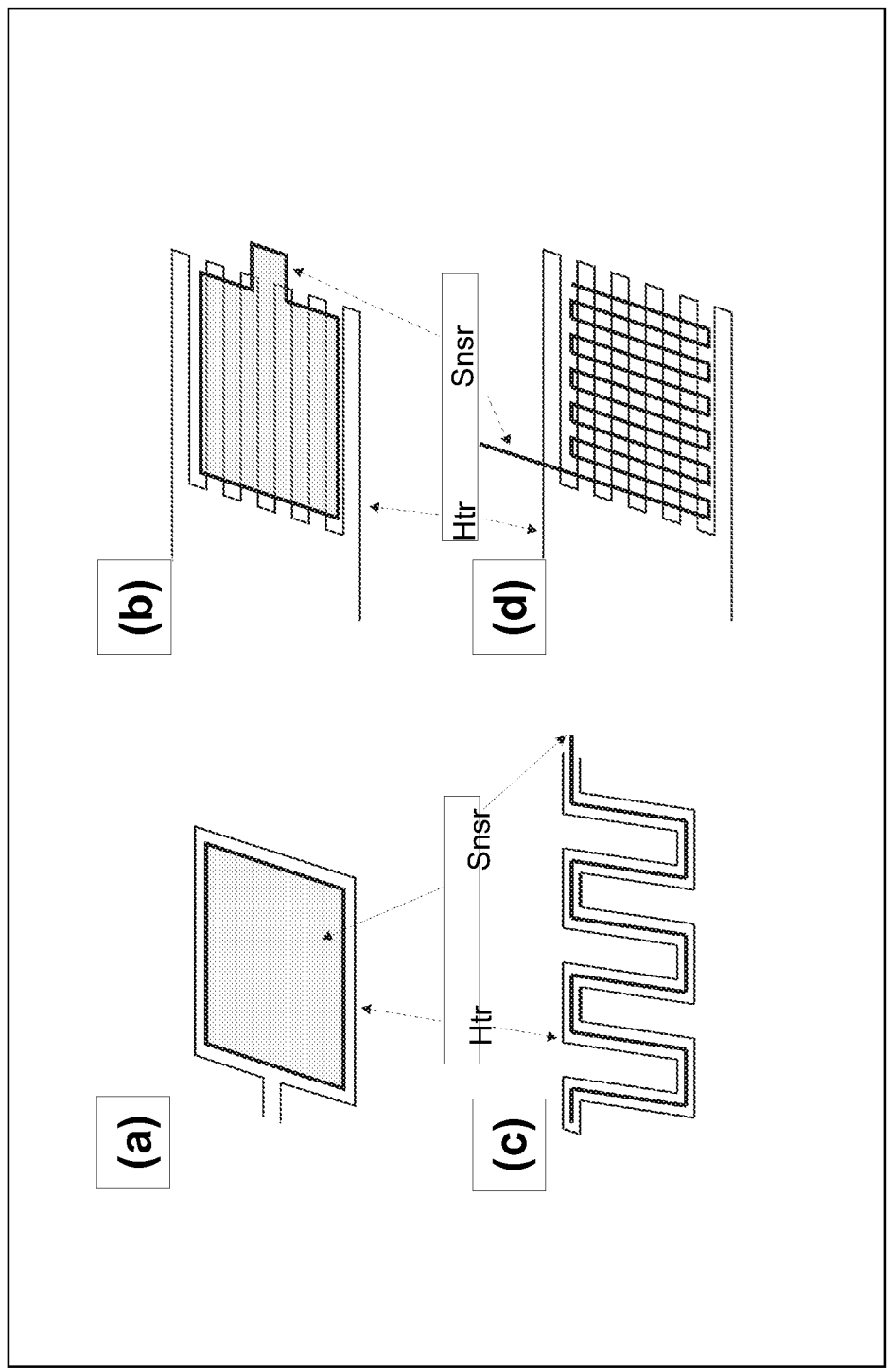
FIGS. 7(a) to 7(d) show four different sensor-heater arrangements in accordance with other embodiments of the invention.

The second electrode Se is connected to a fixed potential, e.g. ground. A heater Htr (temperature setting means) has been provided close, for example underneath, to the first electrode Fe and first sensor dielectric Fsd. What is important is that the heater Htr is provided such that it is thermally coupled to the first electrode Fe and the first sensor dielectric Fsd for setting a temperature of the first interface between the first sensor dielectric Fsd and the analyte in operational use. Providing the heater Htr only near the first electrode Fe is a possible way of creating a temperature difference between said interfaces. Many variations are possible in this respect. Some of these variations are illustrated in FIG. 7. The transistor NM of the sensor has a floating gate, because the connection between gate Gt and first electrode Fe is not galvanically connected to any voltage source. Instead, it is surrounded by insulators such as the gate dielectric, first sensor dielectric Fsd and interconnect dielectric. As explained earlier, in the electrochemical sensor in accordance with the invention it is no longer required to set the DC-potential of the analyte with a reference electrode (or a pseudo-reference electrode). Instead, it is only required to set a working-point of the transducer, i.e. the transistor NM. In this embodiment this is done by implementing a control transistor CT which is connected to the gate Gt for pre-setting its DC-potential. Such control transistor CT merely acts as a switching element receiving a DC-bias-voltage on its input and connected with its output to the gate and being controlled by a control signal on its control input for temporarily transferring this DC-bias-voltage to the gate Gt. The DC-bias-voltage is chosen such that the transistor operates in a proper operating point of its curve. It must be noted that the measurement signal which it receives on its gate is a transient voltage (modulated by the temperature) rather than a DC-voltage.

The major advantage of the EGFET of FIG. 5(a) as compared to the ISFET is that the first electrode Fe is implemented in the top metal layer of the chip and thus 'far away' from the transistor NM. This reduces risk of contamination with, e.g. alkaline ions, such as $Na^+$. Moreover, it allows easy integration with standard CMOS processes. The transistor part of the EGFET acts as the earlier-mentioned transducer in this embodiment.

FIG. 5(b) shows a configuration having two measurement electrodes which are used in a differential way having only one heater. This embodiment will be discussed in as far as it differs from the embodiment in FIG. 5(a). Instead of using a transistor as transducer, a differential amplifier DA is used to measure the potential difference between the first electrode Fe and the second electrode SE. The heater is provided near the first electrode Fe only. The first electrode Fe and the second electrode Se are connected to inputs of the differential amplifier DA. This embodiment may be used as follows. The right sensor is heated/cooled creating a voltage difference between both amplifier inputs. Any (constant) offset between the inputs is not relevant for the measurement, because the measurement signal is conveyed in the "additional" difference resulting from the heating/cooling of the right sensor.

In the embodiments of FIG. 5(a) and FIG. 5(b) the second electrode Se together with the second ion-sensitive dielectric Ssd may be considered as a capacitive reference CR for the first electrode Fe and the first ion-sensitive dielectric Fsd. It is possible to provide a control transistor/switching element for each input of the differential amplifier in the same way as illustrated in FIG. 5(a). Such element can be used to preset the DC-voltages of the inputs (and thereby the electrodes).

FIG. 5(c) shows a configuration having two measurement electrodes which are used in a differential way having two heaters. This embodiment will be discussed in as far as it differs from the embodiment in FIG. 5(b). The main difference is that this embodiment is provided with a heater at each electrode, i.e. the temperature of both electrodes is controlled (but differently) for creating the required temperature difference. This embodiment may be used as follows. First, the temperature of the first electrode Fe is varied while the temperature of the second electrode Se is kept constant (same operation as for simple configuration with only one heater). Measurements are done during this temperature variation, i.e. the potential difference between the first electrode Fe and the second electrode Se is measured for the different temperatures of the first electrode providing the measurement points of the potential-temperature curve. This provides a first slope. Then, the same measurement is done varying the temperature of the second electrode Se while keeping the temperature of the first electrode Fe constant. This provides a second slope. Both obtained slopes are then averaged which may remove any systematic measurement error originating from the heating of a single sensor. Consequently, the measurement accuracy may be increased. In this embodiment it is more difficult to indicate a capacitive reference, because both electrode configurations have a similar function. It could be argued the respective electrodes alternatingly act as a reference and a measurement electrode, respectively. It is possible to provide a control transistor/switching element for each input of the differential amplifier in the same way as illustrated in FIG. 5(a). Such element can be used to preset the DC-voltages of the inputs (and thereby the electrodes).

FIG. 5(d) shows a so-called Electrolyte Semiconductor Insulator (EIS) structure. The Electrolyte Semiconductor Insulator structure comprises a first electrode Fe comprising a conductive contact layer Cl (e.g. metal pad, silicide) onto which a silicon layer Sl is provided. Alternatively, it may be a germanium layer, a silicon-germanium layer, a III-V semiconductor compound, a II-VI semiconductor compound or any other kind of semiconductor compound. On the silicon layer Sl a sensor dielectric Snsd is provided. The stack is similar to a MOS (Metal Oxide Semiconductor) capacitor. It differs there from in that the dielectric/oxide is contacted by the analyte rather than by metal. The flat-band voltage of the EIS capacitor yields information on the pH-value/ion concentration of the analyte. It is determined by C-V (capacitance voltage) measurements or with a constant capacitance method. Normally, both methods require a reference electrode and an electrode to modulate the analyte potential for the capacitance measurements. In this embodiment of the electrochemical sensor in accordance with the invention, however, such reference electrode is no longer required. Instead, a capacitive reference CR similar to the previous embodiments is provided. The capacitive reference CR comprises a second electrode Se provided with a second ion-sensitive dielectric Ssd thereon. In order to form a capacitance, the second electrode Se is arranged to contact the analyte only through the second ion-sensitive dielectric Ssd, in operational use. If leakage is sufficiently small the analyte potential can be set via this capacitive reference, this is done via a voltage source Vsrc connected between the capacitive reference CR and ground in FIG. 5(d) (the overall measurement time must be smaller than the time constant of the change in DC voltage caused by the leakage). Moreover, the AC modulation for the capacitance measurement is applied via the same capacitive reference CR. The DC potential of the analyte is set as follows. When the voltage of the voltage source Vsrc is switched to a different voltage the voltage over the capacitive reference CR changes and thus the potential of the analyte 100 accordingly (the first capacitor $C_{fe}$ and the second capacitor $C_{se}$ that are connected in series via the analyte form a capacitive voltage divider). However, this only applies under ideal conditions without any leakage. In case of leakage the DC potential of the analyte 100 gradually changes due to charge/discharge of the reference capacitor. It is important that in that case the time constant of this charge/discharge must be much higher than the duration of the measurements. In case of the EIS device the (DC) voltage is varied via the reference electrode and also the (sinusoidal) modulation is applied.

Again the temperature at the first dielectric Fsd/first interface is modulated with a heater Htr near, for example underneath, the EIS layer stack. Temperature changes (implying also a change in the temperature difference between the first interface and the second interface) affect the surface potential that subsequently causes a shift in the flat-band voltage. Thus the surface potential is indirectly measured via the flat-band voltage.

More information on the electrolyte-insulator semiconductor structure can be found in the following document:

Shoji Yoshida, Nobuyoshi Hara, and Katsuhisa Sugimoto, "Development of a Wide Range pH Sensor based on Electrolyte-Insulator Semiconductor Structure with Corrosion-Resistant $Al_2O_3$—$Ta_2O_5$ and $Al_2O_3$—$ZrO_2$ Double-Oxide Thin Films.", Journal of The Electrochemical Society, 151 (3) H53-H58 (2004) [REF4]. This document has been incorporated by reference in its entirety.

More information on C-V measurements can be found in the following document:

M. Klein, "CHARACTERIZATION OF ION-SENSITIVE LAYER SYSTEMS WITH A C(V) MEASUREMENT METHOD OPERATING AT CONSTANT CAPACITANCE.", Sensors and Actuators B1 (1-6): p 354-356, JAN 1990 [REF5]. This document has been incorporated by reference in its entirety.

Because of the special measurement principle of the invention the earlier described problems related to the reference electrode and calibration are no longer relevant (or at least to a much smaller degree) for the electrochemical sensor in accordance with the invention. In particular, the embodiments described here can be easily miniaturized and integrated into standard CMOS devices. Only minor additions to a standard processing scheme are necessary. Moreover, these modifications are after all conventional processing has been finished, and before dicing and packaging).

Figure 5:
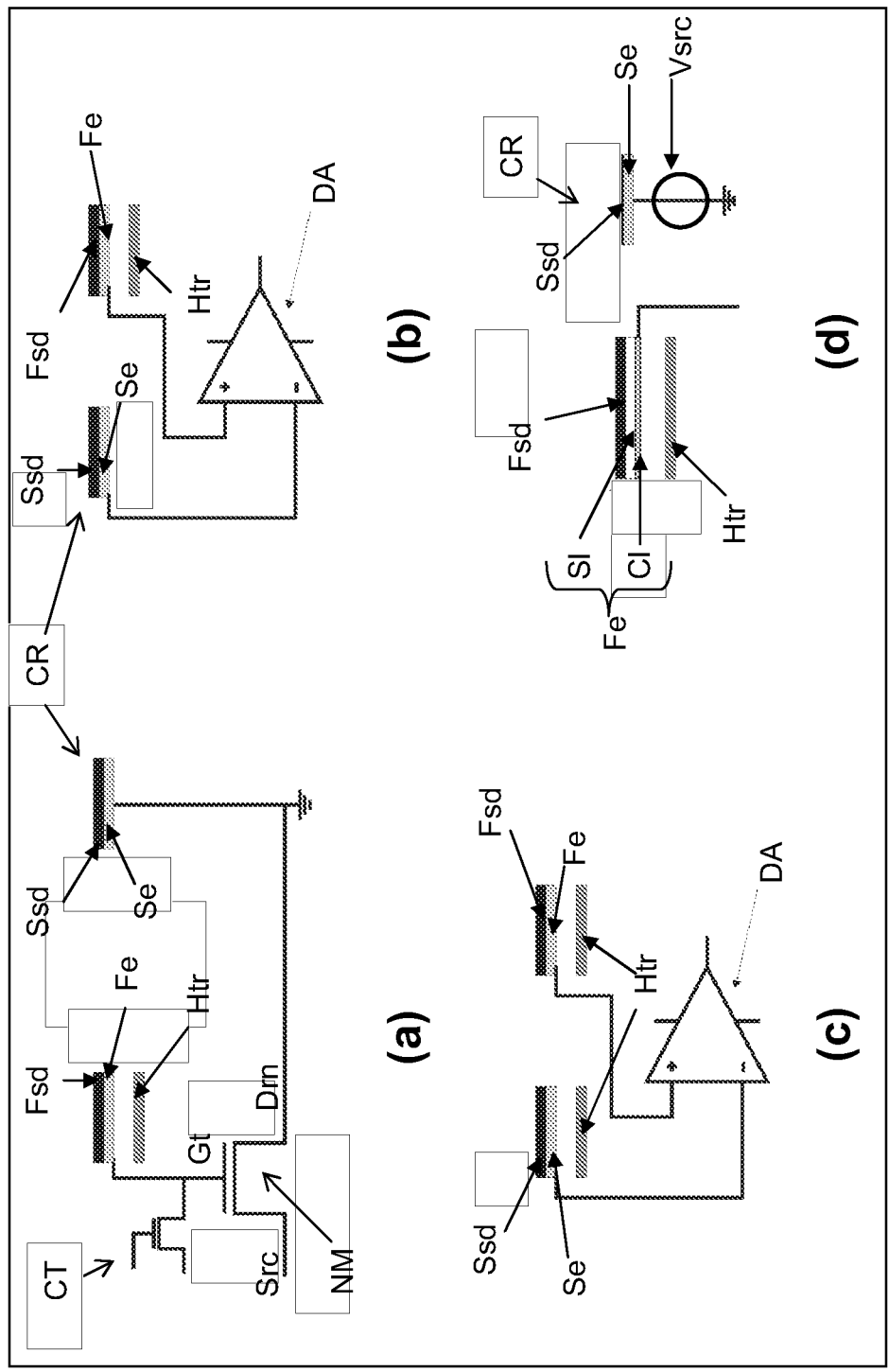
FIGS. 5(a) to 5(d) show four embodiments of the electrochemical sensor in accordance with an embodiment of the invention.
Figure 6:
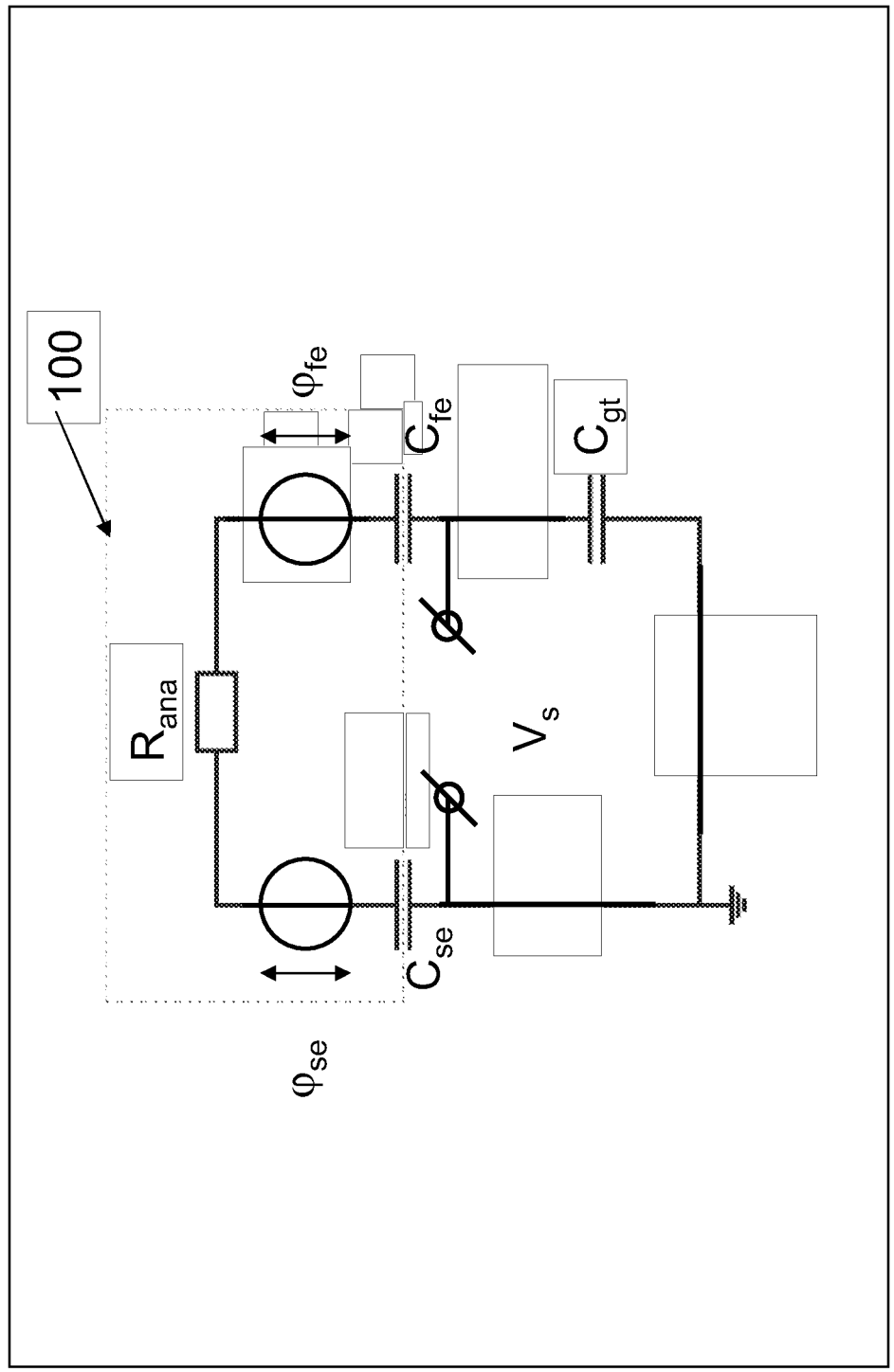
FIG. 6 shows an electrical equivalent-circuit diagram of the electrochemical sensor when in contact with the analyte.

FIG. 6 shows an electrical equivalent-circuit diagram of the electrochemical sensor when in contact with the analyte. This equivalent-circuit is valid for the sensors illustrated in FIGS. 5(a) to 5(c). The invention will be explained on the basis of the equivalent circuit of FIG. 6. The equivalent circuit constitutes the relevant components of the signal path between the electrodes and the transducer. For the sake of simplicity, in the equivalent circuit any interconnect resistance and other parasitic components are ignored. Components that are within the dashed box are "located" within the analyte 100 or formed by the analyte 100, such as the analyte resistance $R_{ana}$. The analyte resistance $R_{ana}$ depends on the charged particle ion concentration in the analyte, the size of the first electrode and second electrode, i.e. this quantity is a spreading resistance. The first electrode and the first ion-sensitive dielectric together form a first electrode capacitance Cfe with the analyte 100. The surface-potential variation that is generated at the first interface between the first ion-sensitive dielectric and the analyte 100 is represented as a first variable voltage source $\phi_{fe}$, i.e. the variable component of the first surface potential that is generated (which depends on the temperature of the first interface and the pH-value of the analyte). The surface-potential variation that is generated at the second interface between the second ion-sensitive dielectric and the analyte 100 is represented as a second variable voltage source $\phi_{se}$, i.e. the variable component of the second surface potential that is generated (which depends on the temperature of the second interface and the pH-value of the analyte). The input capacitance of the transducer, i.e. in this example a field-effect transistor, is represented as a gate capacitance $C_{gt}$ that is connected between the first capacitance $C_{fe}$ and ground.

The invention may be understood as follows. In case the first electrode and the second electrode have exactly the same configuration and the same temperature, i.e. no temperature difference, the surface-potentials generated at the first and second interface are exactly the same. If the respective temperatures of respective first and second interfaces are varied different from each other, the respective surface-potentials become different, i.e. respective variable components of the respective surface potentials $\phi_{fe}$, $\phi_{se}$ are generated. Even more important, as a result of the difference between said different variable components of the respective surface potentials $\phi_{fe}$, $\phi_{se}$, a measurement signal $V_s$ is generated over the gate capacitance $C_{gt}$ of the transducer, which can be measured. The measurement signal thus depends on respective temperatures of the first and second interface and the pH-value of the analyte.

The electric behavior of the equivalent-circuit of FIG. 6 has been simulated for the situation that only the temperature of the first interface is varied (which means that $\phi_{se}$=constant). In this configuration the second electrode forms the earlier mentioned capacitive reference with the analyte. The simulations show that the signal on the gate capacitance $C_{gt}$ is very strong (almost equal to the variation of the surface potential of the first electrode $\phi_{fe}$) if the capacitance of the second electrode $C_{se}$ i much larger than the capacitance of the first electrode $C_{fe}$.

When the simulation was carried out with a first surface-potential variation $\phi_{fe}$ of 10 mV (amplitude) on the first electrode second capacitance $C_{se}$ that is 100 times larger than the first capacitance $C_{fe}$, the following voltage amplitudes were obtained.

$V_s(t)$=9.9 mV (=gate signal amplitude of the transducer), and $V_{Cse}$=0.6 μV (signal amplitude on second capacitor $C_{se}$ (=reference capacitor)).

As can be see, the signal on the second capacitor $C_{se}$ is almost negligible.

So, when the temperature of only one of the interfaces is varied, it is advantageous to make the other interface as large as possible to obtain a larger capacitance (an alternative is to make the dielectric layer thinner on the respective electrode, but that makes the manufacturing process more difficult).

Due to parasitic effects such as leakage it is not possible to control the DC potential of the analyte 100 over a long time with the 'capacitive reference' (second electrode). Therefore the working point of the transducer (extended gate FET etc.) should be set just before the actual measurement. In order to minimize errors the measurement time (heating and read out of transducer signals) must be considerably faster than the drift (caused by leakage which results in change of the analyte potential).

In the electrochemical sensor of FIG. 5(a) the voltage floating gate of the transducer can be pre-charged by temporarily activating (switching "on") the control transistor CT just before the measurement. In order to do so the pre-charge voltage has to be put on the input (source or drain) of the control transistor, and the gate voltage of the control transistor CT has to be set high (in case of an n-type transistor)). During the measurement itself the control transistor must be "off" in order to prevent a shunting of the sensor signal.

In a configuration without control transistors i.e. floating gate, the working point can be set by pre-charging the 'capacitive reference' as earlier described. In that case the 'capacitive reference' (second electrode) is not connected to ground but to a voltage source. Similar configurations with switches such as the 'gate control FET' can also be used in the other systems of FIG. 2 for setting the transducer's working points (not shown).

FIGS. 7(a) to 7(d) show four different sensor-heater arrangements in accordance with other embodiments of the invention. All figures are simplified, in particular for the sensor. For the sensor only the sensor electrodes are shown. In FIG. 7(a) the sensor Snsr is arranged as a large pad, whereas the heater Htr is arranged (in a same plane) around the periphery of the pad. In FIG. 7(b) the heater Htr is arranged under the sensor pad Snsr in the form of a meander. This configuration ensures a more uniform temperature of the sensor. In FIG. 7(c) the sensor Snsr is arranged as a meander structure, and the heater Htr is arranged, in a same plane, as a meander structure on both sides of the sensor Snsr in a river-routing fashion. In FIG. 7(d) the sensor Snsr is arranged as a meander structure. The heater Htr is arranged below the sensor Snsr as a meander structure in a 90°-rotated. The actual arrangement of heater Htr and sensor Snsr may considerably affect the temperature uniformity of the sensor. The person skilled in the art may easily come up with further variations of the sensor Snsr and heater Htr. In any case, what is important is that the heater Htr (temperature settings means) is thermally coupled to the sensor Snsr for enabling the setting of the sensor temperature.

Method of Manufacturing

Sensor manufacturing of the embodiments of FIGS. 5 and 7 follows standard CMOS processing schemes. This is the case for the transducers as well as for most parts of the electrodes (and heater). It is a key asset of the electrochemical sensor in accordance with the invention that all electrodes, including the second electrode/capacitive reference can be easily integrated into the device itself, because it has a similar configuration as the first electrode. If we consider a CMOS process with five metal layers for interconnect the heater can be implemented as a thin metal line (resistive heater) in Metal4 and the electrodes in Metal5 (for the geometries of FIGS. 7(a) and 7(c) both the heater Htr and electrodes can be implemented in Metal5). Metal layers are separated by inter-layer-dielectric (ILD). Standard back-end-of-line processes are used for this, such as (dual)-damascene processing. Depending on the actual interconnect technology aluminum and copper are the most commonly used metals. The only non-standard steps are: i) deposition of the ion-sensitive dielectrics on top of the electrodes in Metal5 and ii) opening of the bondpads. Both steps can be done as the final processing steps before dicing and packaging. Thus no changes are required for the standard processing part of the manufacturing method. The ion-sensitive dielectrics can cover the entire device surface (including the heaters in arrangements in FIGS. 7(a) and 7(c)) thus acting as additional protective layer against the electrolyte. If a scratch protection/passivation stack is used the process steps may involve: opening of the scratch protection (lithography, etch) on top of sensor electrodes and bondpads, uniform deposition of sensor dielectric, removal of sensor dielectric on bond pads.

In order to improve protection, e.g. reduce pin holes, stacks of different dielectrics can be deposited. The actual sensitivity is determined by the final layer in contact with the electrolyte.

Energy Consumption

Despite the use of a heater in some embodiment of the electrochemical sensor in accordance with the invention, the overall energy consumption is low, because the heated volume can be very small. If we consider a sensor having a surface area of 1000 μm2 the overall heat capacity is about 7.4*10-9 J/K. The following assumptions are made for this calculation:

the heater is assumed in Metal4;
the heat propagation to Metal3 and Metal5 are assumed to be identical;
the total thickness of the heated stack is assumed to be around 3.5 μm;
aluminum is used as metal;
siliconoxide is used as intra-metal-dielectric and inter-layer dielectric, and;
the electrolyte itself needs hardly to be heated only at the interface to the dielectric).

Doing ten measurements at ten different temperatures with 1K temperature difference and cool down in between (starting from the equilibrium temperature) requires an overall energy of $3.3*10^{-7}$ J which corresponds to 92 pAh (at 1V). This energy is so small that it does not impose any restriction to the sensor, even not for miniature sensors in autonomous sensors tags powered with a small battery (capacity in the range of 1 mAh). The low-energy consumption is also beneficial for a rapid cool down. The heated volume is very small (3500 μm$^3$). This means that less than 1 μL of analyte is sufficient to act as "reservoir" with constant temperature. This reservoir serves to cool down the sensor to the initial temperature after a heat pulse. The calculation above does not take into account dissipation during the heating process (heat conduction). The required energy to achieve a certain temperature increase may therefore be larger with real devices than the numbers above.

As already described earlier in this description, the invention may also be applied in different application areas, i.e. in de field of molecule sensors (biosensors). FIGS. 8(a) to 8(d) show the manufacturing and operation principle of an electrochemical biosensor in accordance with yet another embodiment of the invention and its principle of operation. The electrochemical biosensor is to a large extent very similar to the already described embodiments of the sensor. Therefore, the biosensor will only be discussed in as far as it differs from the sensor already described. FIG. 8(a) shows such (plain) sensor that has already been described. In this embodiment the ion-sensitive dielectric has been provided as a continuous sensor dielectric layer Snsd that covers both the first electrode Fe and the second electrode Se. In FIG. 8(b) the sensor is modified for turning the sensor into the biosensor. In order to do so the entire surface of the sensor dielectric Snsd is provided with a probe molecule layer Pml. In operational use the probe molecule layer Pml is in direct contact with the analyte. The probe molecule layer Pml is applied such that the sensor dielectric is configured for binding charged target molecules in the analyte. This enables to determine a charged target molecule concentration in the analyte. FIGS. 8(c) and 8(d) illustrate the operation principle of the biosensor. In FIG. 8(c) the sensor is applied in an analyte having biomolecules Bm in it. Biomolecules Bm that match with functional parts of the probe molecule layer Pml bind to the surface and change the surface potential of the sensor. In FIG. 8(d) the analyte is replaced by a measuring solution. This step is optional, which depends on which approach, as discussed below, is chosen. The measuring solution is an electrolyte that does not contain any biomolecules but closes the electrical circuit.

The surface of the sensor dielectric Snsd is functionalized with probe molecules capable of binding to target molecules that have to be detected in the analyte. The functionalized surface may comprise immobilized nucleic acids, e.g. probe-cDNA or mRNA. When the nucleic acid sequence of the (immobilized) probe-cDNA or mRNA is complementary to the nucleic acid sequence of the target DNA (in the analyte), the probe-cDNA or mRNA hybridizes to the DNA fragment and changes the sensor surface potential. Similarly proteins, hormones and various pathogens may be detected by immobilizing the respective antibodies on the sensor surface. Probe-DNA and antibodies may be immobilized using linkers, self assembled monolayer's (SAM), in situ nucleic acid synthesis, etc. In a variation on this embodiment the probe molecules are directly provided on the electrodes. In that embodiment the ion-sensitive dielectric is not required.

The core of the measurement principle of the biosensor is the same as for pH/ion measurement, namely to vary a temperature difference between the first interface and the second interface and measure any change in the potential difference, i.e. output from the transducer. However, due to the different "binding"-mechanism of the biomolecules (the binding is not automatically reversible as is the case for the pH/ion sensor), a slightly modified scheme must be followed. There are multiple approaches possible of which two are discussed below.
Approach 1:

As a first step, a calibration step is performed. In this step a measurement is done using a reference solution of which its content is known. The reference solution is an electrolyte with fixed pH and salt concentration to close the electrical circuit. With "measurement" is meant a measurement in accordance with the invention at least two different temperatures differences (determining at least two different potential differences). The obtained data is saved or stored. This calibration step can be done in a manufacturing environment as part of the manufacturing process, if desired.

As a second step, the analyte 100 is applied to the sensor for a predetermined amount of time. During this time period target molecules are bound to the probe molecule layer Pml.

As a third step, the surface of the sensor is flushed. In this flushing step in principle any solution can do that does not contain target molecules nor remove bound target molecules during flushing.

As a fourth step, another measurement (measurement at least two different temperature differences) is performed on the reference solution. The result of this measurement is compared with the data from the reference measurement. If target molecules have bound to the probe molecule layer Pml they will stay there during flushing and the results from the second measurement will be different form the first. This difference is indicative of the concentration of the target molecules in the analyte 100.
Approach 2:

A more simple approach is to measure constantly during application of the analyte 100. With "measurement" is again meant measurement at least two different temperature differences. As the target molecules slowly bind to the sensor probe molecule layer Pml the sensor readings gradually change. It is important that the measurements at different temperature differences are performed quickly so that the at least two measurements per "measurement" experience approximately the same biomolecule concentration. The difference between measurements right after analyte exposure and measurements after a certain exposure time is indicative of the original concentration of target molecules in the analyte 100.

The biosensor may comprise several sensors (e.g. in an array) functionalized with different probe molecules (deposited by ink jet spotting, etc.) to detect different target molecules in a single measurement run.

The thermo potentiometric principle in accordance with the invention only allows the detection of charged particles, such as ions, as these charged particles attach to the sensor surface and change the surface potential (Nernst equation only applies to ions, pH is a special ion: $H_3O^+$, $OH^-$). Therefore the biosensors in accordance with the invention are also applicable to charged target molecules. Charged target molecules of interest are DNA for example. DNA is known to be charged, although this charge may have many different values. Unlike normal ions, such as $Na^+$-ions, the charge on biomolecules heavily depends on the pH-value of the analyte in which they are dissolved, which makes these charged particles somewhat more special.

The invention thus provides a method of determining a charged particles concentration in an analyte. This method, which still is a potentiometric electrochemical measurement, exploits the temperature dependency of a surface-potential of a measurement electrode. The invention further provides an electrochemical sensor and electrochemical sensor system for enabling to determine a charged particle concentration in an analyte. The invention also provides various sensors which can be used to determine the charged particle concentration, i.e. EGFET's and EIS capacitors.

The invention may be applied in a wide variety of application areas, for example in ion concentration sensors, and in particular in pH-sensors. Further the invention may be applied in miniature sensors integrated into autonomous (RFID) tags. The invention may also be applied in potentiometric sensors with surface modifications, e.g. detection of biomolecules attaching to a sensor surface.

Various variations of the sensor and method in accordance with the invention are possible and do not depart from the scope of the invention as claimed. These variations for example relate to material choice, layer thickness, spatial arrangement of the sensor parts, etc. Also, in the method of determining a charged particle concentration in accordance with an embodiment of the method of the invention, many alterations are possible. Such alterations fall within the normal routine of the person skilled in the art and do not deviate from the inventive concept here disclosed. The most important variations are:

Sensor dielectrics may include materials like: $SiO_2$, $Ta_2O_5$, SiN, $TiO_2$, $HfO_2$, $Al_2O_3$, and similar materials.

Non-dielectric sensor materials can also be used, such as antimony and other metals, polymers, such as Polyaniline, Polypyrrole, Linear Polyethylenimine, Linear Polypropylenimine, and similar materials. These materials may be either in direct contact with the sensor electrode or with a dielectric in between.

A temperature sensor may be implemented near the sensor to accurately determine the temperature at the interface between sensor material (dielectric) and analyte. For example, a thermistor can be realized by an additional thin metal wire surrounding the sensor pad (similar to the arrangement of the heater around the pad in FIG. 6(a)).

Several sensors which are configured for different analytes can be implemented on a single chip, e.g. pH-value and $Na^+$-ion concentration.

An inductive heater may be used instead of a resistive heater.

The heater can be operated in constant-power mode (wherein activation time is adjusted) or in constant-activation-time mode (wherein the power is adjusted).

The sensor capacitance forms a capacitive voltage divider together with the input capacitance of the transducer (e.g. gate capacitance, input capacitance of differential amplifier). In order to improve the signal of the sensor, the sensor capacitance can be increased (it should be preferably larger than the transducer's input capacitance). The capacitance can be increased by making a the sensor area larger, or by making the sensor dielectric layer thinner A peltier element may be used as a cooler (temperature setting means).

The sensor dielectric may be provided with or exchanged with an ion-exchange resin. Ion-exchange resins are based on special organic polymer membranes which contain a specific ion-exchange substance (resin). This is the most widespread type of ion-specific electrode. Usage of specific resins allows preparation of selective electrodes for tens of different ions, both single-atom or multi-atom. They are also the most widespread electrodes with anionic selectivity. However, such electrodes have low chemical and physical durability as well as "survival time". An example is the potassium selective electrode, based on valinomycin as an ion-exchange agent.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage. Throughout the Figures, similar or corresponding features are indicated by same reference numerals or labels.

The invention claimed is:

1. An electrochemical sensor for determining a charged particle concentration in an analyte, the electrochemical sensor comprising:
a first electrode with a first ion-sensitive dielectric provided thereon, the first electrode being configured to contact the analyte via the first ion-sensitive dielectric to obtain a first interface between the first ion-sensitive dielectric and the analyte, wherein the first ion-sensitive dielectric is further provided with a probe molecule layer comprising probe molecules;
a second electrode with a second ion-sensitive dielectric provided thereon, the second electrode being configured to contact the analyte via the second ion-sensitive dielectric to obtain a second interface between the second ion-sensitive dielectric and the analyte, and
a controller configured to measure a potential difference between the first electrode and the second electrode using at least two different values of a temperature difference between the first interface and the second interface to obtain at least two measurement points of a surface-potential versus interface-temperature curve.

2. The electrochemical sensor as claimed in claim 1, wherein the controller comprises:
a temperature setting device configured to set the temperature difference between the first interface and the second interface to said at least two different values.

3. The electrochemical sensor as claimed in claim 1, wherein a semiconductor layer is provided between the first electrode and the first ion-sensitive dielectric.

4. The electrochemical sensor as claimed in claim 1, further comprising:
a transducer for measuring said potential difference.

5. The electrochemical sensor as claimed in claim 4, wherein the transducer comprises:
a differential amplifier connected with its inputs to said first electrode and said second electrode or a transistor connected with its gate to said first electrode and with its source to the second electrode.

6. The electrochemical sensor as claimed in claim 1, wherein the controller is coupled to the first electrode and configured to initiate the measuring of the potential difference between the first electrode and the second electrode at said at least two different values to obtain at least two measurement points of the surface-potential versus interface-temperature curve.

7. The electrochemical sensor as claimed in claim 6, wherein the controller comprises:
a temperature sensor configured to measure the at least two different values of the temperature difference, and wherein the controller is configured to initiate the measuring of the surface-potential at a desired value of the temperature difference.

8. The electrochemical sensor as claimed in claim 6, wherein the controller comprises:

a storage device configured to store the respective measured values of the surface-potential.

9. The electrochemical sensor of claim 8, wherein the storage device is configured to store the respective values of the temperature difference between the first interface and the second interface.

10. The electrochemical sensor as claimed in claim 6, wherein the controller comprises:
a processor device configured to calculate the charged particle concentration from the at least two measurement points of said surface-potential versus interface-temperature curve.

11. The electrochemical sensor as claimed in claim 1, wherein the probe molecule layer is in direct contact with the analyte in operational use, the first ion-sensitive dielectric thereby being configured to bind charged target molecules to enable determination of a charged target molecule concentration in the analyte.

12. The electrochemical sensor of claim 11, wherein the probe molecules are antibodies.

13. The electrochemical sensor of claim 11, wherein the probe molecules are DNA/RNA strands.

14. A semiconductor device comprising the electrochemical sensor as claimed in claim 1, the semiconductor device comprising:
a semiconductor body; and
at least one interconnect layer, wherein the first electrode and the second electrode are located in the at least one interconnect layer, and the controller is located in the semiconductor body and/or the at least one interconnect layer.

15. An RF-ID tag comprising the electrochemical sensor as claimed in claim 1.

16. The electrochemical sensor of claim 1, wherein the second electrode is a capacitive reference.

17. The electrochemical sensor of claim 1, wherein at least three measurement points of the surface-potential versus interface-temperature curve are used to determine a straight fitting line.

18. The electrochemical sensor of claim 1, wherein the first electrode and the second electrode comprise identical layers and materials.

19. The electrochemical sensor of claim 1, wherein a heater is arranged around a periphery of the electrochemical sensor.

20. The electrochemical sensor of claim 1, wherein a heater is arranged under the electrochemical sensor in a form of a meander.

21. A method of determining a charged particle concentration in an analyte, the method comprising:
determining at least two measurement points of a surface-potential versus interface-temperature curve, wherein the interface temperature is obtained from a temperature difference between a first interface between a first ion-sensitive dielectric and the analyte and a second interface between a second ion-sensitive dielectric and the analyte, and the surface-potential is obtained from a potential difference between a first electrode and a second electrode onto which said first ion-sensitive dielectric and said second ion-sensitive dielectric are respectively provided; and
calculating the charged particle concentration from locations of the at least two measurement points of said curve.

22. The method as claimed in claim 21, wherein the step of determining of said curve comprises sub-steps of:
setting the temperature difference to a first value;
determining a first value of the potential difference, wherein the first value of the temperature difference and the first value of the potential difference together define a first respective one of the measurement points of said curve;
setting the temperature difference to a second value different from the first value; and
determining a second value of the potential difference, wherein the second value of the temperature difference and the second value of the potential difference together define a second respective one of the at least two measurement points of said curve.

\* \* \* \* \*